US010081636B2

(12) United States Patent
Mkrtchyan et al.

(10) Patent No.: US 10,081,636 B2
(45) Date of Patent: Sep. 25, 2018

(54) METHOD FOR CATALYTIC PREPARATION OF HYDROMORPHONE, HYDROCODONE, AND OTHER OPIATES

(71) Applicant: Cody Laboratories, Inc., Cody, WY (US)

(72) Inventors: Gnel Mkrtchyan, Cody, WY (US); Iouri Voitsekhovski, Cody, WY (US); Scott Michaels, Cody, WY (US)

(73) Assignee: Cody Laboratories, Inc., Cody, WY (US)

( * ) Notice: Subject to any disclaimer, the term of this patent is extended or adjusted under 35 U.S.C. 154(b) by 0 days.

(21) Appl. No.: 15/644,266

(22) Filed: Jul. 7, 2017

(65) Prior Publication Data

US 2018/0009821 A1 Jan. 11, 2018

Related U.S. Application Data

(60) Provisional application No. 62/359,815, filed on Jul. 8, 2016.

(51) Int. Cl.
*C07D 489/02* (2006.01)
*C07D 489/04* (2006.01)
*B01J 31/24* (2006.01)

(52) U.S. Cl.
CPC ........ *C07D 489/02* (2013.01); *B01J 31/2414* (2013.01); *B01J 2231/52* (2013.01); *B01J 2531/822* (2013.01)

(58) Field of Classification Search
CPC ... C07D 489/02; C07D 489/04; A61K 31/485
USPC ...................................... 546/45, 44; 514/282
See application file for complete search history.

(56) References Cited

U.S. PATENT DOCUMENTS

| | | | |
|---|---|---|---|
| 2,544,291 A | 3/1951 | Baizer | |
| 2,577,947 A | 12/1951 | Baizer | |
| 5,847,142 A | 12/1998 | Mudryk et al. | |
| 5,866,161 A * | 2/1999 | Childers | A61K 9/0004 424/465 |
| 5,981,751 A | 11/1999 | Mudryk et al. | |
| 6,512,117 B1 | 1/2003 | Harclerode et al. | |
| 6,589,960 B2 | 7/2003 | Harclerode et al. | |
| 6,887,999 B1 | 5/2005 | Likhotvorik | |
| 6,946,556 B1 | 9/2005 | Likhotvorik et al. | |
| 7,321,038 B2 | 1/2008 | Wang et al. | |
| 7,323,565 B2 | 1/2008 | Wang et al. | |
| 7,399,858 B2 | 7/2008 | Wang et al. | |
| 7,399,859 B1 * | 7/2008 | Kouznetsov | C07D 489/02 546/44 |
| 7,625,918 B2 | 12/2009 | Hagen et al. | |
| 7,692,013 B2 | 4/2010 | Antonini | |
| 7,928,234 B2 | 4/2011 | Carroll et al. | |
| 7,999,104 B2 | 8/2011 | Carroll et al. | |
| 8,293,907 B2 | 10/2012 | Wang et al. | |
| 8,383,815 B2 | 2/2013 | Gindelberger | |
| 8,399,671 B2 | 3/2013 | Orr et al. | |
| 8,563,725 B2 | 10/2013 | Jiang et al. | |
| 8,921,556 B2 | 12/2014 | Giguere et al. | |
| 8,962,841 B2 | 2/2015 | Hudlicky et al. | |
| 9,012,468 B2 | 4/2015 | Wang et al. | |
| 9,040,705 B2 | 5/2015 | Wang et al. | |
| 9,273,060 B2 * | 3/2016 | Matharu | C07D 489/02 |
| 9,556,108 B2 | 1/2017 | Liao et al. | |
| 2005/0124811 A1 | 6/2005 | Wang et al. | |
| 2007/0293676 A1 | 12/2007 | Antonini | |
| 2009/0022798 A1 | 1/2009 | Rosenberg et al. | |
| 2010/0261904 A1 | 10/2010 | Wang et al. | |
| 2010/0261905 A1 | 10/2010 | Gindelberger | |
| 2010/0261906 A1 | 10/2010 | Haar, Jr. et al. | |
| 2013/0035488 A1 | 2/2013 | Jones et al. | |
| 2016/0137655 A1 | 5/2016 | Matharu et al. | |
| 2016/0168159 A1 | 6/2016 | Tracey et al. | |

FOREIGN PATENT DOCUMENTS

| | | |
|---|---|---|
| DE | 365683 | 12/1922 |
| DE | 380919 | 9/1923 |
| DE | 607 931 | 1/1935 |
| DE | 617 238 | 10/1935 |
| DE | 623 821 | 1/1936 |
| WO | 96/08253 A1 | 3/1996 |
| WO | 98/05667 A1 | 2/1998 |
| WO | 2005/100361 A1 | 10/2005 |
| WO | 2012/003468 A1 | 1/2012 |
| WO | 2013/019825 A1 | 2/2013 |
| WO | 2015/011474 A1 | 1/2015 |
| WO | 2015/134003 A1 | 9/2015 |
| WO | 2016/067054 A1 | 5/2016 |

OTHER PUBLICATIONS

Hydrocodone Bitartrate, Official Monographs, 1 page (Official until Jul. 1, 2008).
Hydrocodone, Official Monographs, The United States Pharmacopeia The National Formulary 2 pages (Jan. 1, 1990).
International Search Report and Written Opinion for Application No. PCT/US2017/041181 dated Sep. 6, 2017.
Kashiwabara, K. et al., "Chiral Recognition in Catalytic Hydrogenation of α-Acylaminoacrylic Acids by Cationic Rhodium(I) Complexes of Chiral Aminophsphines Derived from (R,R)-1,2_Cyclohexanediamine or (R)-1,2-Propanediamine," Bull. Chem. Soc. Jpn., vol. 53, No. 8, pp. 2275-2280 (Aug. 1980).
McGrath, D. et al., "The Mechanism of Aqueous Ruthenium(II)-Catalyzed Olefin Isomerization," Organometallics, vol. 13, pp. 224-235 (1994).
Metal Scavengers Selection Guide, http://www.silicycle.com/products/metal-scavengers/siliabond-metal-scavengers-selectio . . ., 5 pages (Date Retrieved Jun. 2016).

(Continued)

*Primary Examiner* — Charanjit Aulakh

(74) *Attorney, Agent, or Firm* — Merchant & Gould, P.C.

(57) ABSTRACT

Methods are provided for efficient preparation of hydromorphone or hydrocodone by redox isomerization of morphine or codeine allylic alcohols, respectively, using transition metal aminophosphine catalysts formed in situ.

40 Claims, 2 Drawing Sheets

(56) References Cited

OTHER PUBLICATIONS

Moss, "Nomenclature of Fused and Bridged Fused Ring Systems," Pure & Appl. Chem. vol. 70, No. 1, pp. 143-216 (1998).
Neue Arzneimittel, Archiv der Pharmazie, vol. 261, No. 2, pp. 139-143 (1923).
Product Specification, Chlorobis(cyclooctene)iridium(I)dimer—97%, Product No. 377155, Sigma-Aldrich, (Date Retrieved Jun. 2016).
Product Specification, Chlorobis(cyclooctene)iridium(I),dimer—98%, Product No. 302473, Sigma-Aldrich, (Date Retrieved Jun. 2016).
Product Specification, Di-µchlorotetraethylene dirhodium(I), Product No. 656763, Sigma-Aldrich (Date Retrieved Jun. 2016).
Hydrocodone Bitartrate—DEA Schedule II, Cat. No. H4516, Sigma, 1 page (Revised Jun. 1997).
SiliaBond® Metal Scavengers, SiliCycle Inc., 20 pages (Date Retrieved Feb. 2017).
Svoboda, P. et al., "Reduction of Substituted Cyclohexanones by 2-Propanol in the Presence of Aminophosphine-Rhodium(I) Complexes," Collection Czechoslov. Chem. Commun., vol. 22, pp. 2177-2181 (1977).
Ahlsten et al., "Rhodium-catalysed isomerisation of allylic alcohols in water at ambient temperature", Green Chemistry, vol. 12, No. 9, 1 Jan. 2010, p. 1628-1633.

* cited by examiner

METHOD FOR CATALYTIC PREPARATION OF HYDROMORPHONE, HYDROCODONE, AND OTHER OPIATES

CROSS-REFERENCES TO RELATED APPLICATIONS

This application claims the benefit under 35 U.S.C. § 119(e) of U.S. provisional application No. 62/359,815, filed on Jul. 8, 2016, the disclosure of which is herein incorporated by reference in its entirety.

BACKGROUND OF THE INVENTION

Field of the Invention

Methods are provided for efficient preparation of hydromorphone or hydrocodone by redox isomerization of morphine or codeine allylic alcohols, respectively, using transition metal aminophosphine catalysts formed in situ. Homogenous transition metal aminophosphine catalyst complexes are prepared in situ and are employed to readily isomerize cyclic allylic alcohols under mild conditions.

Description of the Related Art

Hydromorphone and hydrocodone are semi-synthetic narcotics used as analgesics and antitussive drugs. Both compounds can be prepared by transition metal catalyzed isomerization of morphine and codeine, respectively.

Redox isomerization of allylic alcohols to the corresponding ketones catalyzed by soluble transition metal complexes is a well-documented process (see, for example, McGrath, et al. Organometallics, 1994, 13, 224 and references cited therein).

Morphine and codeine are allylic alcohols, and application of homogeneous catalysis for the isomerization of these compounds to hydromorphone and hydrocodone are disclosed in WO2015/011474, U.S. Pat. No. 9,040,705, U.S. Pat. No. 7,399,859, U.S. Pat. No. 5,847,142, WO 98/05667, and US 2005/0124811 A1. However, these references demonstrate that the transition metal catalyst must be present in at least 0.05 mol %, 0.1 mol %, 1 mol % or greater to achieve efficient transformation.

It is desirable to further reduce the amount of transition metal catalyst required to reduce costs and streamline purification procedures. Thus, a need exists for new efficient catalysts capable of converting morphine to hydromorphone and codeine to hydrocodone.

The present disclosure further provides methods of synthesizing catalysts of formula (III), and methods of use in transforming codeine to hydrocodone and morphine to hydromorphone. The catalysts may also be used to isomerize other allylic alcohols to their corresponding ketones.

SUMMARY OF THE INVENTION

Efficient methods are provided for preparing a compound of formula (I) or a pharmaceutically acceptable salt and/or solvate thereof

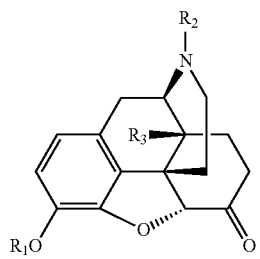

wherein $R_1$ is selected from H, or optionally substituted $C_{1-18}$ alkyl, $C_{2-18}$ alkenyl, $C_{2-18}$ alkynyl, or $C_{3-18}$ cycloalkyl, or $R^P$, wherein $R^P$ is a hydroxy protecting group; $R_2$ is selected from H, or optionally substituted $C_{1-18}$ alkyl, $C_{2-18}$ alkenyl, $C_{2-18}$ alkynyl, or $C_{3-18}$ cycloalkyl, or $R^Q$, wherein $R^Q$ is a nitrogen protecting group; and $R_3$ is selected from H, —OH, or optionally substituted $C_{1-18}$ is alkyl, $C_{1-18}$ alkoxy, $C_{2-18}$ alkenyl, $C_{2-8}$ alkynyl, or $C_{3-18}$ cycloalkyl, or —$OR^P$, wherein $R^P$ is a hydroxy protecting group, the method comprising exposing a compound of formula (II)

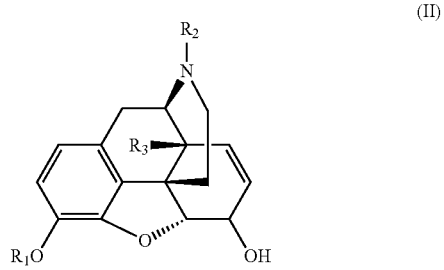

wherein $R^1$, $R^2$ and $R^3$ are as defined above, to a transition metal complex catalyst of formula (III)

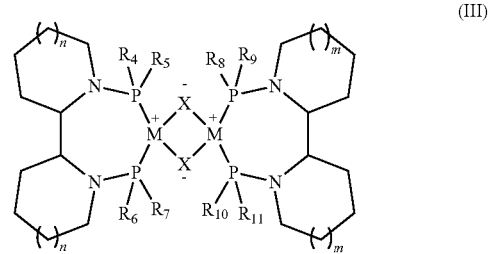

wherein M is selected from Rh or Ir; each X is independently H, —OH, halo, alkoxy, aryloxide, an anion or a solvent molecule; $R_4$, $R_5$, $R_6$, $R_7$, $R_8$, $R_9$, $R_{10}$ and $R_{11}$ are independently selected from H and optionally substituted aryl, heterocyclic, or cycloalkyl; n is 0 or 1; and m is 0 or 1.

In some embodiments, a compound of formula (III) is employed wherein X is halo; and $R_4$, $R_5$, $R_6$, $R_7$, $R_8$, $R_9$, $R_{10}$ and $R_{11}$ are each optionally substituted aryl. In preferred embodiments, the compound of formula (III) is provided wherein X is halo; M is Rh; $R_4$, $R_5$, $R_6$, $R_7$, $R_8$, $R_9$, $R_{10}$ and $R_{11}$ are each phenyl; m is 1; and n is 1.

Thus, in some embodiments, methods are provided for efficient preparation of hydromorphone or hydrocodone by redox isomerization of morphine or codeine allylic alcohols, respectively, using transition metal aminophosphine catalysts of formula (III) formed in situ.

Other opiates such as naloxone, naltrexone, oxycodone and oxymorphone may be prepared by analogous methods.

In some embodiments, the compounds of formula (I) and/or formula (II) comprise wherein $R_1$ is H or $C_{1-6}$ alkyl; $R_2$ is H, $C_{1-6}$ alkyl, $C_{2-6}$ alkenyl, or $C_{3-6}$ cycloalkyl; and $R_3$ is H, or —OH. In specific embodiments, the compound of formula (I) comprises wherein $R_1$ is H or $CH_3$; $R_2$ is $CH_3$, allyl, or cyclopropylmethyl; and $R_3$ is H or —OH.

In some embodiments, the compound of formula (I) is selected from hydromorphone ($R_1$=H, $R_2$=$CH_3$, $R_3$=H); hydrocodone ($R_1$=$CH_3$, $R_2$=$CH_3$, $R_3$=H); oxycodone ($R_1$=$CH_3$, $R_2$=$CH_3$, $R_3$=OH); naloxone ($R_1$=H, $R_2$=allyl, $R_3$=OH); naltrexone ($R_1$=H, $R_2$=cyclopropylmethyl, $R_3$=OH); oxymorphone ($R_1$=H, $R_2$=$CH_3$, $R_3$=H); or a pharmaceutically acceptable salt thereof.

In some embodiments, the compounds of formula (I) and/or formula (II) comprise wherein $R_1$ is H or $CH_3$; $R_2$ is $CH_3$; and $R_3$ is H or —OH.

In one specific embodiment, the compounds of formula (I) and/or formula (II) comprise wherein $R_1$ is H or $CH_3$; $R_2$ is $CH_3$; and $R_3$ is H.

In another specific embodiment, the compounds of formula (I) and/or formula (II) comprise wherein $R_1$ is H; $R_2$ is $CH_3$; and $R_3$ is H. In some embodiments, methods are provided for preparing hydromorphone from morphine by exposing the morphine to a transition metal aminophosphine complex catalyst of formula (III).

In a further specific embodiment, the compounds of formula (I) and/or formula (II) comprise wherein $R_1$ is $CH_3$; $R_2$ is $CH_3$; and $R_3$ is H. In some aspects, the compound of formula (II) is codeine base or a hydrate thereof or concentrated poppy straw-codeine (CPS-C). In a specific embodiment, methods are provided for preparing hydrocodone or a pharmaceutically acceptable salt and/or hydrate thereof by exposing the codeine to a transition metal aminophosphine complex catalyst of formula (III).

In some embodiments, a method is provided for forming a compound of formula (I) or a salt and/or solvate thereof comprising exposing a compound of formula (II) to 0.05-0.3 mol % of the transition metal aminophosphine complex catalyst of formula (III) to transform the compound of formula (II) into the compound of formula (I) or salt and/or solvate thereof. In some embodiments, the transformation of compound (II) is efficiently converted into the compound of formula (I) in greater than 97%, 99%, 99.5%, or 99.9% conversion by HPLC.

In some embodiments, methods are provided herein for the transformation of compound (II) into the compound of formula (I) comprising dissolving the compound of formula (II) or a salt thereof in a solvent selected from water, methanol, ethanol, isopropanol, n-propanol, methylene chloride/methanol, tetrahydrofuran, acetone, or any combination thereof prior to or during exposing to a compound of formula (III).

In some embodiments, methods are provided comprising adding a pharmaceutically acceptable acid to the compound of formula (I) to form the pharmaceutically acceptable salt of the compound of formula (I) or the solvate thereof. In some aspects, the pharmaceutically acceptable acid is added to the base form of the compound of formula (I) without isolating the base form. In some embodiments, the pharmaceutically acceptable acid is an inorganic acid selected from the group consisting of hydrochloric acid, hydrobromic acid, sulfuric acid, nitric acid, and phosphoric acid; or an organic acid selected from the group consisting of acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. In some embodiments, a method is provided further comprising isolating the pharmaceutically acceptable salt of the compound of formula (I) or the solvate thereof by crystallization.

In specific embodiments, methods are provided for forming a compound of formula (I) or pharmaceutically acceptable salt or solvate thereof comprising adding 0.05-0.3 mol % of the compound of formula (III) to the compound of formula (II), wherein the resulting pharmaceutically acceptable salt of the compound of formula (I) or solvate thereof is isolated in greater than 80%, 85% or 90% yield compared to the compound of formula (II); and in some aspects, the purity of the isolated pharmaceutically acceptable salt of the compound of formula (I) or the solvate thereof is greater than 99%, 99.5%, or 99.8% by HPLC.

In some embodiments, a method is provided for catalytically converting codeine into hydrocodone or morphine into hydromorphone comprising exposing the codeine or morphine to at least one transition metal aminophosphine complex catalyst of formula (III)

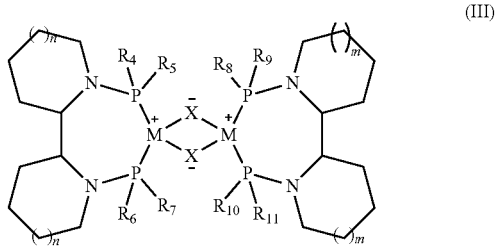

(III)

wherein M is selected from Rh or Ir; each X is independently H, —OH, halo, alkoxy, aryloxide, an anion or a solvent molecule; $R_4$, $R_5$, $R_6$, $R_7$, $R_8$, $R_9$, $R_{10}$ and $R_{11}$ are independently selected from H and optionally substituted aryl, heterocyclic, or cycloalkyl; n is 0 or 1; and m is 0 or 1.

In some embodiments, the method comprises exposing the codeine or morphine to 0.05-0.3 mol % of the at least one transition metal aminophosphine complex catalyst of formula (III) to form a reaction mixture. In some aspects, the reaction mixture is heated to a temperature selected from 35° C. to 100° C., 50 to 90° C., or 60 to 80° C., or reflux temperature. In some aspects, the reaction mixture is heated for a period of 0.5 to 48 hours, 1 to 36 hours or 5 to 30 hours, wherein the transformation of compound (II) into the compound of formula (I) is greater than 97%, 98%, 99%, 99.5%, or 99.9% by HPLC. In some embodiments the heating of the reaction mixture is performed under increased pressure in a reactor for a reduced period of time of about 0.5 hours to about 4 hours, about 1 hour to about 3 hours, or about 2.5 hours to obtain at least 97%, 98%, 99%, 99.5%, or 99.9% conversion of compound (II) into the compound of formula (I). In some embodiments, the increased pressure is selected from about from about 3 psi to about 50 psi, about 5 psi to about 25 psi, or about 10 psi.

In some embodiments, the codeine starting material is concentrated poppy straw-codeine (CPS-C). In some aspects, the CPS-C is used without purification. CPS-C can contain up to 0.5% each of oripavine and thebaine. Although these impurities are not transformed during reaction methods provided herein, they were not detected in the resulting product hydrocodone bitartrate or hydrate thereof during spiking studies. CPS-C can also contain up to 0.5% 14-hydroxycodeine which can be transformed to oxycodone in the present reaction methods. However, neither 14-hydroxycodeine nor oxycodone were detected in the resulting hydrocodone bitartrate or hydrate thereof during spiking studies.

In some aspects the method comprises dissolving the stating material comprising morphine or codeine in a solvent selected from water, methanol, ethanol, isopropanol, n-propanol, methylene chloride/methanol, tetrahydrofuran, acetone, or a suitable mixture thereof, prior to exposing to the transition metal aminophosphine complex catalyst of formula (III). In some embodiments, the method provides hydrocodone bitartrate hemipentahydrate having not more than 0.05%, 0.03%, 0.02%, 0.015% or 0.01% codeine impurity by HPLC.

In some embodiments, methods are provided for generating a transition metal aminophosphine complex catalyst of formula (III) in situ by mixing an aminophosphine of formula (IVa) and/or (IVb)

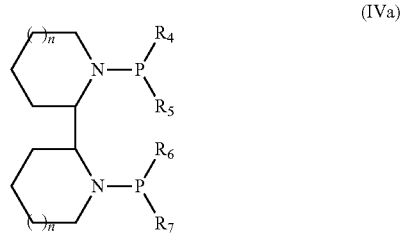

(IVa)

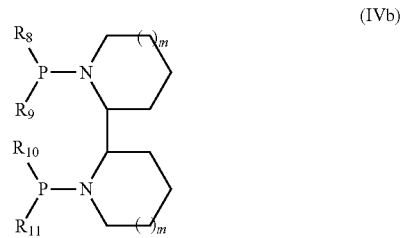

(IVb)

in a solvent with a transition metal precursor of formula (V)

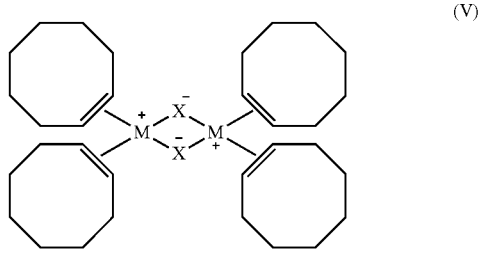

(V)

wherein M is selected from Rh or Ir; each X is independently H, —OH, halo, alkoxy, aryloxide, an anion or a solvent molecule; $R_4$, $R_5$, $R_6$, $R_7$, $R_8$, $R_9$, $R_{10}$ and $R_{11}$ are independently selected from H and optionally substituted aryl, heterocyclic, or cycloalkyl; n is 0 or 1; and m is 0 or 1. In preferred embodiments, M is Rh or Ir; X is halo; $R_4$, $R_5$, $R_6$, $R_7$, $R_8$, $R_9$, $R_{10}$ and $R_{11}$ are aryl; n is 1; and m is 1. In some embodiments, the compound of formula (V) has X=Cl, as shown in the compound (Va), shown in FIG. 2. In a specific preferred embodiment, M is Rh; X is Cl; $R_4$, $R_5$, $R_6$, $R_7$, $R_8$, $R_9$, $R_{10}$ and $R_{11}$ are phenyl.

In some embodiments, the solvent for preparing the transition metal aminophosphine complex catalyst of formula (III) is selected from toluene, xylenes, 4-xylene, 3-xylene, 2-xylene, p-cymene, hexane and methylcyclohexane. In a specific aspect the solvent is toluene. In a specific preferred aspect the solvent is oxygen-free solvent, such as oxygen-free toluene.

In some embodiments, methods are provided for forming a pharmaceutically acceptable salt of a compound of formula (I) and/or solvate thereof comprising exposing a compound of formula (II) or a salt thereof to a transition metal aminophosphine complex catalyst of formula (III) to form a compound of formula (I), and further comprising adding a pharmaceutically acceptable acid to the compound of formula (I) to form the pharmaceutically acceptable salt of the compound of formula (I) or the solvate thereof. In some embodiments, the method comprises adding a pharmaceutically acceptable acid to the base form of the compound of formula (I) without isolating the base form. In some embodiments, the pharmaceutically acceptable acid is an inorganic acid selected from the group consisting of hydrochloric acid, hydrobromic acid, sulfuric acid, nitric acid, and phosphoric acid; or an organic acid selected from the group consisting of acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. In some embodiments, the method further comprises isolating the pharmaceutically acceptable salt of the compound of formula (I) or the solvate thereof by crystallization, wherein the pharmaceutically acceptable salt of the compound of formula (I) or the solvate thereof is isolated in greater than 80%, 85% or 90% yield compared to the compound of formula (II). In some aspects, the purity of the isolated pharmaceutically acceptable salt of the compound of formula (I) or the solvate thereof is greater than 99%, 99.5%, or 99.8%. In some embodiments, the isolated pharmaceutically acceptable salt of the compound of formula (I) or the solvate thereof is provided having not more than 0.05%, 0.03%, 0.02%, 0.015% or 0.01% starting compound of formula (II) by HPLC.

In some embodiments, a pharmaceutically acceptable salt of the compound of formula (I) or the solvate thereof is provided prepared by a method comprising seed bed crystallization. In some embodiments, the seed bed crystallization comprises dissolving or diluting the base form of the compound of formula (I) in a water miscible solvent; adding the pharmaceutically acceptable acid to form a solution; mixing the solution with a first slurry of a pharmaceutically acceptable salt of the compound of formula (I) or solvate thereof in a solvent system comprising a water miscible solvent and water to form a second slurry; and isolated a crystalline precipitate of the pharmaceutically acceptable salt of the compound of formula (I) or solvate thereof from the second slurry.

DETAILED DESCRIPTION OF THE INVENTION

Definitions

Figure 1:
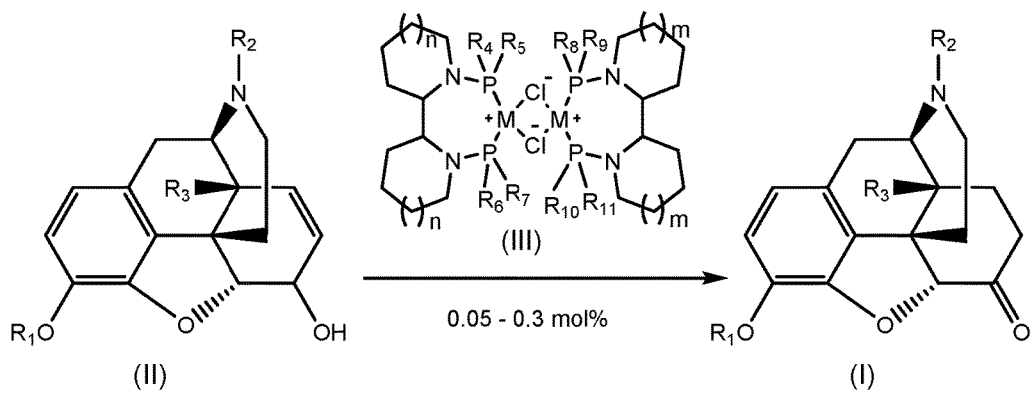
FIG. 1 shows a representative scheme for efficient preparation of a compound of formula (I) from a compound of formula (II) in a single step by exposure to a relatively low mol % of a transition metal aminophosphine complex catalyst of formula (III), as shown where X is Cl.

The term "alkyl" refers to straight or branched chain alkyl groups having one or more carbon atoms which may be saturated, unsaturated or partially unsaturated; "substituted alkyl" refers to alkyl groups further bearing one or more substituents such as hydroxy, alkoxy, mercapto, aryl, cycloalkyl, heterocyclic, halogen, trifluoromethyl, cyano, nitro, amino, carboxyl, carbamate, sulfonyl, sulfonamide and the like. Unless otherwise specified, "alkyl" refers to $C_{1-18}$ alkyl. In some aspects, alkyl may be selected from methyl ($-CH_3$), ethyl ($-CH_2CH_3$), propyl ($-CH_2CH_2CH_3$), isopropyl ($CH(CH_3)_2$), butyl ($-CH_2CH_2CH_2CH_3$), sec-butyl ($-CH(CH_3)CH_2CH_3$), isobutyl ($-CH_2CH(CH_3)_2$), tert-butyl ($-C(CH_3)_3$), or $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ straight or branch chained alkyl groups. In some embodiments, the alkyl is selected from $C_{1-18}$ alkyl, $C_{1-12}$ alkyl, $C_{1-9}$ alkyl, $C_{1-6}$ alkyl, $C_{1-4}$ alkyl, or $C_{1-3}$ alkyl. The term medium alkyl refers to $C_{1-9}$ alkyl; and lower alkyl refers to $C_{1-4}$ alkyl.

The term "alkenyl" refers to a refers to straight or branched chain alkyl groups having two or more carbon atoms comprising at least one C=C double bond which otherwise may be saturated, unsaturated or partially unsaturated, and "substituted alkenyl" refers to alkenyl groups further bearing one or more substituents such as hydroxy, alkoxy, mercapto, aryl, cycloalkyl, heterocyclic, halogen, trifluoromethyl, cyano, nitro, amino, carboxyl, carbamate, sulfonyl, sulfonamide and the like. Unless otherwise specified, alkenyl refers to $C_{2-18}$ alkenyl. In various aspects, alkenyl may be selected from vinyl, allyl, 1-propenyl, 2-propenyl, isopropenyl, 1-butenyl, 2-butenyl, 3-butenyl, sec-butenyl, isobutenyl, isoprenyl, $C_{2-9}$, $C_{2-6}$, $C_{2-5}$, $C_{2-4}$, $C_{2-3}$ or $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ straight or branch chained alkenyl groups. In aspects, the alkenyl is a medium size alkenyl of $C_{2-9}$, or a small alkenyl having $C_{2-4}$.

The term "alkynyl" refers to a refers to straight or branched chain alkyl groups having two or more carbon atoms comprising at least one carbon-carbon triple bond which otherwise may be saturated, unsaturated or partially unsaturated. Unless otherwise specified, alkynyl refers to $C_{2-18}$ alkynyl. "Substituted alkynyl" refers to alkynyl groups further bearing one or more substituents such as hydroxy, alkoxy, mercapto, aryl, cycloalkyl, heterocyclic, halogen, trifluoromethyl, cyano, nitro, amino, carboxyl, carbamate, sulfonyl, sulfonamide and the like. In aspects, the alkynyl is a medium size alkynyl of $C_{2-9}$, or $C_{2-6}$ alkynyl, or a small alkynyl having $C_{2-4}$.

The term "alkoxy" refers to the formula $-OR$ wherein R is an alkyl as is defined above, such as "$C_{1-18}$ alkoxy", "$C_{1-9}$ alkoxy", "$C_{1-6}$ alkoxy", or "$C_{1-4}$ alkoxy", including but not limited to methoxy, ethoxy, n-propoxy, 1-methylethoxy(isopropoxy), n-butoxy, iso-butoxy, sec-butoxy, and tert-butoxy, and the like.

The term "cycloalkyl" refers to cyclic ring-containing groups containing in the range of 3 to 14 carbon atoms in the ring system, which may be a fused or an unfused single ring system, which may be saturated, or partially unsaturated, and "substituted cycloalkyl" refers cycloalkyl groups further bearing one or more substituents as set forth above. In some aspects, cyloalkyl groups may be selected from cyclopropyl, cyclobutyl, cyclopenyl, cyclohexyl, cycloheptyl, cyclooctyl, cyclononyl or cyclodecyl groups.

The term "aryl" refers to aromatic ring systems having 6 to 14 carbon atoms in the ring system, (which may be fused such as in napthylene, azulene, anthracene, or phenanthrene). In some embodiments, the aryl group has 6 to 10 carbon atoms. "Substituted aryl" refers to aryl groups further bearing one or more substituents as set forth above. Aryl groups in compounds of formula (III) include phenyl and substituted phenyl groups.

The term "aryloxide" or "aryloxy" refers to RO— in which R is an aryl as is defined above, such as "$C_{6-10}$ aryloxy", including but not limited to phenyloxy.

The term "heterocyclic" or "heterocyclyl" refers to cyclic (i.e., ring-containing) groups, which may be fused, containing one or more heteroatoms (e.g., N, O, S, or the like) as part of the ring structures, and having 3 to 14 carbon atoms in the ring system, which may be saturated, unsaturated or partially unsaturated, and "substituted heterocyclic" refers to heterocyclic groups further bearing one or more substituents as set forth above. Heterocyclyls may be joined together in a fused, bridged or spiro-connected fashion. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

The term "halogen" refers to fluoride, chloride, bromide, or iodide groups. In some aspects, the halo atoms are selected from Cl, I and Br.

Typical anions include $BF_4$, $PF_6$, $ClO_4$, $CHO_2$, $C_2O_4$, $CF_3CO_2$, $CF_3SO_3$, $CH_3CO_2$, $ArCO_2$, $CH_3SO_3$, $OCOCF_3$, p-tolylSO$_3$, $HSO_4$ and $H_2PO_4$.

Examples of alcohol or phenol protecting groups within the definition of $R^P$ include ethers (such as methoxymethyl, benzyloxymethyl, 2-(trimethylsilyl)ethoxymethyl ether, tetrahydropyranyl, phenacyl, allyl, triethylsilyl, t-butyldimethylsilyl), esters (such as acetate, pivaloate, benzoate), carbonates (such as benzyl, methyl) and sulfonates (such as methanesulfonate, toluenesulfonate).

Examples of amine protecting groups within the definition of $R^Q$ include carbamates (such as methyl, 2,2,2-trichloroethyl, 2-methylsilyl, triethylsilyl, t-butyl, benzyl), amides (such as formyl, acetyl, benzoyl, cyclobutyl), sulfonates and amino acetal derivatives.

The term "optionally substituted" refers to wherein the moiety may be unsubstituted; or substituted as set forth above; or substituted with a halo, $C_{1-6}$ alkyl, $C_{2-6}$ alkenyl, $C_{2-6}$ alkynyl, or $C_{3-7}$ cycloalkyl group.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. The "pharmaceutically acceptable acids" useful for preparing the pharmaceutically acceptable acid addition salts may be selected from inorganic acids or organic acids. Inorganic acids from which pharmaceutically acceptable acid addition salts can be derived include, for example, hydrochloric acid, hydrobromic acid, sulfuric acid, nitric acid, phosphoric acid, and the like. Organic acids from which pharmaceutically acceptable acid addition salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The term "solvate" refers to the compound formed by the interaction of a solvent and a compound described herein or salt thereof. Suitable solvates are pharmaceutically acceptable solvates including hydrates, or a solvates of any other solvent provided herein.

Methods

Methods are provided for preparing a compound of formula (I) or a pharmaceutically acceptable salt or solvate thereof,

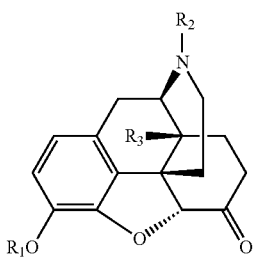

(I)

wherein $R_1$ is selected from hydrogen, or optionally substituted $C_{1-8}$ is alkyl, $C_{2-18}$ alkenyl, $C_{2-18}$ alkynyl, or $C_{3-18}$ cycloalkyl, or $R^P$, wherein $R^P$ is a hydroxy protecting group; $R_2$ is selected from hydrogen, or optionally substituted $C_{1-8}$ is alkyl, $C_{2-18}$ alkenyl, $C_{2-18}$ alkynyl, or $C_{3-18}$ cycloalkyl, or $R^Q$, wherein $R^Q$ is a nitrogen protecting group; and $R_3$ is selected from hydrogen, —OH, or optionally substituted $C_{1-8}$ is alkyl, $C_{1-18}$ alkoxy, $C_{2-18}$ alkenyl, $C_{2-8}$ alkynyl, or $C_{3-18}$ cycloalkyl, or —$OR^P$, wherein $R^P$ is a hydroxy protecting group. In some embodiments, the compound of formula (I) or salt or solvate comprises wherein $R_1$ is hydrogen or $C_{1-6}$ alkyl; $R_2$ is hydrogen, $C_{1-6}$ alkyl, $C_{2-6}$ alkenyl, or $C_{3-6}$ cycloalkyl; and $R_3$ is hydrogen, or —OH.

In some embodiments, the compound of formula (I) or salt or solvate comprises wherein $R_1$ is hydrogen or methyl; $R_2$ is methyl, allyl, or cyclopropylmethyl; and $R_3$ is hydrogen or —OH. In some embodiments, the compound of formula (I) or salt or solvate comprises wherein $R_1$ is hydrogen or methyl; $R_2$ is methyl; and $R_3$ is hydrogen or —OH. In some specific embodiments, the compound of formula (I) or salt or solvate comprises wherein $R_1$ is hydrogen or methyl; $R_2$ is methyl; and $R_3$ is hydrogen. In one specific embodiment, the compound of formula (I) or salt or solvate comprises wherein $R_1$ is hydrogen; $R_2$ is methyl; and $R_3$ is hydrogen. In another specific embodiment, the compound of formula (I) or salt or solvate thereof comprises wherein $R_1$ is H; $R_2$ is methyl; and $R_3$ is OH. In another specific embodiment, the compound of formula (I) or salt or solvate comprises wherein $R_1$ is methyl; $R_2$ is methyl; and $R_3$ is hydrogen. In some embodiments, the compound of formula (I) or salt or hydrate thereof is selected from hydrocodone, hydromorphone, oxymorphone, or oxycodone.

Methods are provided for transforming a compound of formula (II) or a salt thereof into a compound of formula (I) or a pharmaceutically acceptable salt or solvate thereof, as defined herein, wherein

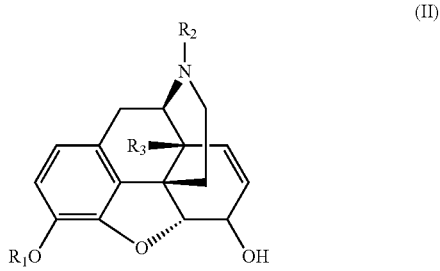

(II)

wherein $R_1$ is selected from hydrogen, or optionally substituted $C_{1-18}$ alkyl, $C_{2-18}$ alkenyl, $C_{2-18}$ alkynyl, or $C_{3-18}$ cycloalkyl, or $R^P$, wherein $R^P$ is a hydroxy protecting group; $R_2$ is selected from hydrogen, or optionally substituted $C_{1-18}$ is alkyl, $C_{2-18}$ alkenyl, $C_{2-18}$ alkynyl, or $C_{3-18}$ cycloalkyl, or $R^Q$, wherein $R^Q$ is a nitrogen protecting group; and $R_3$ is selected from hydrogen, —OH, or optionally substituted $C_{1-18}$ is alkyl, $C_{1-18}$ alkoxy, $C_{2-18}$ alkenyl, $C_{2-8}$ alkynyl, or $C_{3-18}$ cycloalkyl, or —$OR^P$, wherein $R^P$ is a hydroxy protecting group. In some specific embodiments, the compound of formula (II) is selected from codeine, morphine, or 14-hydroxycodeine. In one embodiment, the compound of formula (II) is codeine. In another embodiment, compound of formula (II) is codeine from concentrated poppy straw-codeine (CPS-C). In a further embodiment, the compound of formula (II) is morphine. In one specific aspect, the compound of formula (II) is morphine. In another specific aspect, the compound of formula (II) is 14-hydroxycodeine.

Methods are provided for preparation of compounds according to formula I comprising exposing a compound of formula II to a transition metal aminophosphine complex catalyst according to formula III:

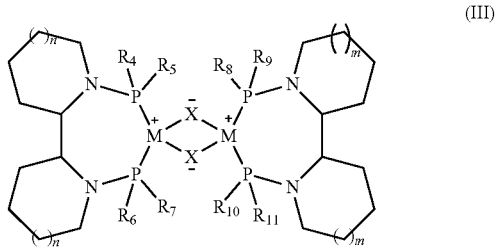

(III)

wherein M is Rh or Ir; each X is independently H, —OH, halo, alkoxy, aryloxy, an anion or a solvent molecule; $R_4$, $R_5$, $R_6$, $R_7$, $R_8$, $R_9$, $R_{10}$ and $R_{11}$ are independently selected from H and optionally substituted aryl, heterocyclic, or cycloalkyl; n is 0 or 1; and m is 0 or 1.

In some embodiments, the transition metal aminophosphine complex catalyst of formula III is a rhodium aminophosphine complex catalyst where M is Rh. In one embodiment, a rhodium aminophosphine complex catalyst according to formula III is provided, wherein each M is Rh; each X is halo; $R_4$, $R_5$, $R_6$, $R_7$, $R_8$, $R_9$, $R_{10}$ and $R_{11}$ are each independently optionally substituted aryl; n is 1 and m is 1. In some embodiments, X is Cl. In a specific embodiment, a rhodium aminophosphine complex catalyst according to formula III is provided, wherein each M is Rh; each X is $C_1$; $R_4$, $R_5$, $R_6$, $R_7$, $R_8$, $R_9$, $R_{10}$ and $R_{11}$ are each independently phenyl; n is 1; and m is 1.

In some embodiments, the transition metal aminophosphine complex catalyst of formula III is an iridium aminophosphine complex catalyst where M is Ir. In one embodiment, a iridium aminophosphine complex catalyst according to formula III is provided, wherein each M is Ir; each X is halo; $R_4$, $R_5$, $R_6$, $R_7$, $R_8$, $R_9$, $R_{10}$ and $R_{11}$ are each independently optionally substituted aryl; n is 1 and m is 1. In some embodiments, X is Cl. In a specific embodiment, an iridium aminophosphine complex catalyst according to formula III is provided, wherein each M is Ir; each X is $C_1$; $R_4$, $R_5$, $R_6$, $R_7$, $R_8$, $R_9$, $R_{10}$ and $R_{11}$ are each independently phenyl; n is 1; and m is 1.

In another embodiment, the transition metal aminophosphine complex catalyst according to formula III is generated in situ and used to efficiently catalyze a redox isomerization of a compound of formula II to form a compound of formula I, using only 0.05-0.3 mol % of catalyst compared to the compound of formula II.

In one embodiment, an improved method is provided for transforming a compound of formula (II) into a compound of formula (I) or a pharmaceutically acceptable salt or solvate thereof in a single pot reaction, the improvement comprising exposing the compound of formula (II) to 0.05-0.3 mol % of a transition metal aminophosphine catalyst complex of formula (III) to obtain greater than 97%, 98%, 99%, or 99.5% transformation by HPLC, wherein the compounds of formulas (I), (II), and (III) are as provided herein.

Catalyst Preparation

Transition metal complex catalysts according to formula (III) are typically prepared by mixing a transition metal precursor with an aminophosphine precursor in an oxygen free environment.

For example, rhodium aminophosphine complex catalysts for this process are conveniently prepared by treatment of commercially available rhodium precursor such as an ethylene or cyclooctene rhodium complex with approximately two molar equivalents of an aminophosphines of formula (IVa) and/or (IVb), wherein $R_4$, $R_5$, $R_6$, $R_7$, $R_8$, $R_9$, $R_{10}$ and $R_{11}$, m and n are as defined above in a suitable solvent. The catalyst complex is typically prepared under an inert gas, for example, under a nitrogen or argon atmosphere using standard Schlenk technique.

In some embodiments, the aminophosphine of formula (IVa) and/or (IVb) is selected from where each of $R_4$, $R_5$, $R_6$, $R_7$, $R_8$, $R_9$, $R_{10}$ and $R_{11}$ is optionally substituted aryl, n is 1, and m is 1. In some embodiments, the compound of formula (IVa) or (IVb) is selected from 1,1'-bis(diphenylphosphino)-2,2'-bipiperidine, (2S,2'S)-1,1'bis(diphenylphosphino)-2,2'-bipiperidine, (2R,2'R)-1,1'bis(diphenylphosphino)-2,2'-bipiperidine, 1,1'-bis(diphenylphosphino)-2,2'-bipyrrolidine, (2R,2'R)-1,1'-bis(diphenylphosphino)-2,2'-bipyrrolidine, or (2S,2'S)-1,1'-bis(diphenylphosphino)-2,2'-bipyrrolidine.

In some embodiments, the transition metal precursor is selected from chlorobis(cyclooctene)rhodium(I) dimer $[ClRh(COE)_2]_2$, chlorobis(ethylene)rhodium(I) dimer [Rh$(C_2H_4)_2Cl]_2$, or chlorobis(cyclooctene)iridium(I) dimer, (Sigma-Aldrich). In some embodiments, the transition metal precursor is a compound according to formula (V), wherein M is selected from Rh or Ir. In specific embodiments, the transition metal precursor is a compound of formula (V) where M is Rh. In a specific aspect, the transition metal precursor is chlorobis(cyclooctene)rhodium(I) dimer [ClRh$(COE)_2]_2$. In some embodiments, the transition metal precursors may be purchased from Sigma-Aldrich Co., St. Louis, Mo., Strem Chemicals Inc., Newburyport, Mass., Colonial Metals, Inc., Elkton, Md., or American Elements, Los Angeles, Calif.

Suitable solvents for catalyst complex preparation include toluene, xylenes, 4-xylene, 3-xylene, 2-xylene, p-cymene, hexane and methylcyclohexane. In some embodiments, the solvent is an anhydrous solvent. In some aspects, the solvent is not an anhydrous solvent. In some aspects, the solvent is sparged with nitrogen to diminish the amount of dissolved oxygen prior to combining with the ethylene or cyclooctene rhodium complex and the aminophosphine. In some aspects, the solvent is an oxygen free solvent. In some embodiments, the solvent is sparged with nitrogen or argon for at least about 15 minutes, at least about 30 minutes, at least about 45 minutes, or at least about 1 hour, or from 15 min to 15 h, 30 min to 6 h, or 1 h to 4 h.

In some embodiments, a transition metal aminophosphine catalyst of formula (III) is provided by a method comprising mixing a transition metal precursor with an aminophosphine dimer according to formula (IVa) and/or (IVb) in a solvent. In some embodiments, the catalyst is prepared at a temperature selected from 0-50° C., 5-45° C., 15 to 35° C., or ambient temperature. In some embodiments, the catalyst is prepared by mixing a transition metal precursor with an aminophosphine of formula (IVa) and/or (IVb) in a suitable solvent under nitrogen or argon atmosphere for a period of time from 5 min to 4 h, 15 min to 3 h, or 30 min to 90 min.

Figure 2:
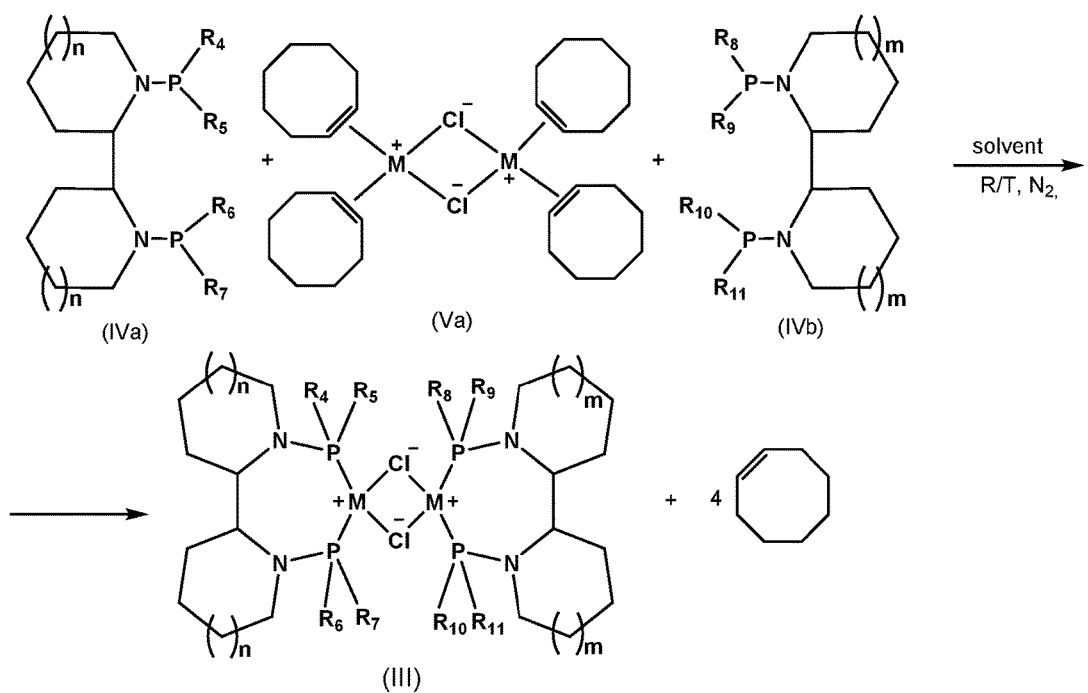
FIG. 2 shows a representative scheme for in situ generation of a transition metal aminophosphine complex catalyst according to formula (III), as shown where X is Cl.

For example, as illustrated generically in FIG. 2, a rhodium-aminophosphine complex catalyst of formula (III) is prepared by adding a compound of formula (V), e.g., chlorobis (cyclooctene) rhodium(1), dimer [(Rh$(COE)_2Cl]_2$ $(C_{32}H_{56}Cl_2Rh_2)$ (717.50 g/mol) [e.g., 24.4 g. 34.0 mmol] and 1,1'-bis(diphenylphosphino)-2,2'-bipiperidine $(C_{34}H_{38}N_2P_2)$ (536.626 g/mol) [e.g., 36.7 g, 68.4 mmol] to toluene [e.g., approximately 2000 mL] with agitation.

Redox Isomerization of Allylic Alcohol

In one embodiment, the catalyst complex is employed in situ in redox isomerization of the cyclic allylic alcohol compound of formula II to form the saturated ketone of formula (I) in a single step.

In some embodiments, a suitable solvent for carrying out the redox isomerization of the cyclic allylic alcohol of formula II is selected from methanol, ethanol, isopropanol, n-propanol, isobutyl alcohol, methylene chloride/methanol, tetrahydrofuran, acetone, or mixtures thereof. In some embodiments, a suitable solvent is an alcohol or a mixture of an alcohol and water. In specific embodiments, the solvent is ethanol or methanol. In other embodiments, the solvent for carrying out the redox isomerization of the allylic alcohol is not toluene.

In some aspects, a base is added to the reaction mixture to enhance the solubility of the compound of formula (II). In some aspects, the optional base is an alkoxide such as a sodium, lithium or potassium alkoxide. In some embodiments, the optional base is selected from sodium methoxide, sodium ethoxide, sodium n-propoxide, sodium isopropoxide, sodium t-butoxide, potassium methoxide, potassium ethoxide, potassium n-propoxide, potassium isopropoxide, potassium t-butoxide, lithium methoxide, lithium ethoxide, lithium n-propoxide, lithium isopropoxide, and lithium t-butoxide.

In some embodiments, the rhodium aminophosphine complex catalysts according to formula (III) are exceptionally efficient at catalyzing the redox isomerization of the allylic alcohol moiety of the compound of formula (II) such that a minimal amount of the complex catalyst may be employed. In some embodiments, the complex catalyst is used at a loading of 0.01-2 mol %, 0.02-1 mol %, or 0.05-0.3 mol % compared to the compound of formula (II). In some embodiments, efficient conversion to a compound of formula (III) is achieved using less than 0.2 mol % or less than 0.1 mol % rhodium aminophosphine complex catalyst. In some embodiments, the efficient transformation into a compound of formula (I) the transformation of compound (II) into the compound of formula (I) is achieved in greater than 97%, 99%, 99.5%, or 99.9% by HPLC with a catalyst loading of 0.05-0.3 mol %.

In some embodiments, the aminophosphine complex catalysts according to formula (III) is generated in situ and added to the solution of the compound of formula (II) under nitrogen or argon atmosphere to form a reaction mixture. In some embodiments, the reaction mixture is heated to a temperature of from 35° C. to 100° C., 50 to 90° C., or 60 to 80° C., or reflux temperature, for a period of 0.5 to 48 hours, 1 to 36 hours or 5 to 30 hours. In some embodiments, greater than 95%, 97%, 98%, 99%, or 99.5% conversion to a compound of formula (I) is observed by HPLC in less than 30 hours, less than 24 h, less than 10 h, or less than 2 h after addition of the aminophosphine complex catalyst to the compound of formula (II).

In some embodiments, purity of product and intermediate compounds, reaction progress, and transformation of starting compounds is assessed by any technique known in the art. For example, purity or transformation may be assessed by HPLC, LC/MS, qNMR, or another suitable scientifically valid assay method. In one embodiment, purity is assessed by HPLC. In another embodiment, percent transformation is assessed by HPLC.

In some embodiments, a method is provided for transforming morphine to hydromorphone, or codeine to hydrocodone, or 14-hydroxycodeine to oxycodone in the presence of a compound according to formula (III). For example, the transition metal aminophosphine complex catalyst of formula (III) allows for efficient preparation of hydrocodone base from codeine base, or hydromorphone base from morphine base, or oxycodone base from 14-hydroxycodeine base in a single step.

In one embodiment, hydrocodone base is prepared from codeine base in a single step by exposing the codeine to a transition metal aminophosphine complex catalyst of formula (III). In one embodiment, hydrocodone base is prepared from concentrated poppy straw-high codeine (CPS-C) without purification of the starting material in a single step by exposing the CPS-C to a transition metal aminophosphine complex catalyst of formula (III). In some embodiments, the transition metal aminophosphine complex catalyst of formula (III) is generated in situ, then added to a solution of the CPS-C.

In another embodiment, hydromorphone base is prepared from morphine base in a single step by exposing the morphine base to a transition metal aminophosphine complex catalyst of formula (III).

In another embodiment, oxycodone base is prepared from 14-hydroxycodeine base in a single step by exposing the 14-hydroxycodeine base to a transition metal aminophosphine complex catalyst of formula (III).

In one method, morphine/codeine/14-hydroxycodeine is transformed to hydromorphone/hydrocodone/oxycodone in the presence of at least one catalyst of the present disclosure. Isomerization of morphine can optionally be done in the presence of a strong base such as sodium methoxide (NaOMe), which deprotonates the phenolic moiety of morphine/hydromorphone and thus increases the solubility of these species in the reaction mixture. In one aspect, complete isomerization of morphine/codeine normally requires less than 1 hour in boiling methanol when 1 mol % of these catalysts is used. However, in another aspect, relatively low 0.05-0.3 mol % complex catalyst may be employed to achieve greater than 95% conversion.

In one embodiment, a method is provided for preparing hydrocodone bitartrate hemipentahydrate from codeine in greater than 90% yield using less than 0.2 mol % of the rhodium aminophosphine complex catalyst. CPS-C is heated to reflux in denatured ethanol or methanol or methanol/water under nitrogen or argon, then less than 0.2 mol % of the in situ aminophosphine rhodium complex catalyst in toluene solution is added, and the mixture is refluxed for not less than 1 hour. The resulting slurry is cooled to below reflux and tartaric acid is added to form a clear solution. The clear solution is allowed to crystallize to return greater than 90% yield of hydrocodone bitartrate hemipentahydrate. The hydrocodone bitartrate hemipentahydrate product purity is typically greater than 99.5% by HPLC with not more than 0.05% codeine impurity.

In one embodiment, a method is provided for preparing hydrocodone bitartrate from concentrated poppy straw-codeine (CPS-C) without purification of the CPS-C by using the transition metal aminophosphine complex catalyst of formula (III). In some embodiments, hydrocodone bitartrate hemipentahydrate is isolated in greater than 85% yield using less than 0.3 mol %, less than 0.2 mol %, or less than 0.1 mol % of the rhodium aminophosphine complex catalyst. CPS-C is heated to reflux in denatured ethanol or methanol under nitrogen, then less than 0.1 mol % of the in situ transition metal aminophosphine complex catalyst in toluene solution is added, and the mixture is refluxed for not less than 1 hour. The resulting slurry is cooled to below reflux temperature and tartaric acid is added to form a clear solution. The clear solution is treated with a stationary phase metal scavenger (about 5% relative to the codeine). The scavenger is filtered and the product was allowed to crystallize to return greater than 85% yield of hydrocodone bitartrate hemipentahydrate. The hydrocodone bitartrate hemipentahydrate product purity is typically greater than 97%, greater than 99%, or greater than 99.5% by HPLC with not more than 0.05% codeine impurity.

In a specific embodiment, hydrocodone bitartrate or a hydrate thereof is provided by a method comprising exposing concentrated poppy straw-codeine (CPS-C) without purification of the CPS-C to the transition metal aminophosphine complex catalyst of formula (III) under increased reactor pressure. In some embodiments, hydrocodone bitartrate hemipentahydrate is isolated in greater than 85% yield using less than 0.3 mol %, less than 0.2 mol %, or less than 0.1 mol % of the rhodium aminophosphine complex catalyst. CPS-C is heated to reflux in a solvent such as denatured ethanol or methanol under nitrogen or argon, then less than 0.1 mol % of the in situ transition metal aminophosphine complex catalyst in toluene solution is added, and the mixture is refluxed for a period of from about 1 h to about 3 h, or about 2.5 h, under increased reactor pressure of from about 3 psi to about 50 psi, about 5 psi to about 25 psi, or about 10 psi to reduce reflux time from about 4 h without increased reactor pressure to about 2.5 hour with increased reactor pressure to obtain at least about 95%, 97%, 98%, 99%, 99.5%, or 99.8% conversion of codeine to hydrocodone by HPLC.

In one embodiment, a method is provided for preparing oxycodone base from 14-hydroxycodeine base in a single step using the transition metal aminophosphine complex catalyst of formula (III). In some embodiments, less than 0.3 mol %, or less than 0.2 mol % of the transition metal aminophosphine catalyst is employed to obtain greater than 80% yield of oxycodone base. 14-hydroxycodeine base is heated to reflux in methanol or ethanol under oxygen free conditions. The solution is cooled to below reflux temperature, and the previously prepared transition metal aminophosphine complex catalyst is added to the solution and the mixture is refluxed for not less than 5 hours. In some aspects, the oxycodone base crystallizes on cooling to return greater than 80% yield and better than 99.5% purity based on HPLC analysis. In some embodiments, the oxycodone base may be purified by any known means such as recrystallization, or may be treated with a pharmaceutically acceptable acid to form a pharmaceutically acceptable salt or solvate thereof.

In one embodiment, a method is provided for preparing hydromorphone base from morphine base using the transition metal aminophosphine complex catalyst of formula (III). In some embodiments, less than 0.3 mol %, less than 0.2 mol % or less than 0.1 mol % of the rhodium aminophosphine complex catalyst is employed to obtain hydromorphone base in greater than 80% yield in a single step with greater than 97%, 98%, or preferably greater than 99% purity by HPLC. In some embodiments, morphine base and sodium methoxide are added to a solvent selected from methanol or ethanol to form a solution. The solution is then heated to and held at reflux for not less than 30 minutes. The solution is cooled to 5-15° C. below reflux temperature, and the previously prepared rhodium-aminophosphine complex catalyst is added to the solution. The mixture is refluxed for not less than 12 h, cooled and crystallized to return hydromorphone in greater than 80% yield, at greater than 99% purity by HPLC.

Catalyst Removal

In one embodiment, following preparation of a compound according to formula I, the transition metal catalyst or degradant thereof is removed from the reaction mixture by precipitation, filtration, phase extraction, crystallization and/or recrystallization. In some embodiments, the catalyst is separated from the reaction mixture by crystallization and/or recrystallization of the compound of formula I, or pharmaceutically acceptable salt thereof, from the reaction mixture or from an appropriate solvent. In some embodiments, a metal scavenger is not employed.

In another embodiment, following preparation of a compound according to formula I, the catalyst is removed from the reaction mixture prior to crystallization by exposing the reaction solution to a metal scavenger. The metal scavenger may be a solution phase metal scavenger or a stationary phase metal scavenger. In some aspects, the metal scavenger is a stationary phase metal scavenger. In some embodiments, the metal scavenger is bound to a stationary phase. The stationary phase may be selected from any typical stationary phase known in the art of chromatography. The stationary phase is not soluble in the suitable solvent for carrying out the redox isomerization. In some embodiments, the stationary phase comprises a silica based stationary phase.

In some embodiments, a metal scavenger is optionally employed to remove the transition metal scavenger or a degradant thereof from the reaction mixture or solution comprising the compound of formula (I), or the pharmaceutically acceptable salt thereof. The metal scavenger binds to the transition metal catalyst or degradant thereof to form a scavenger-metal complex. In some embodiments, the scavenger-metal complex is removed from the reaction mixture by precipitation, filtration, or by binding of the transition metal complex or degradant to the metal scavenger attached to a stationary phase. In some embodiments, the metal scavenger attached to a stationary phase is employed in a batch method, where a slurry is prepared and filtered after a set period of time. In some embodiments, the metal scavenger is employed in a continuous process such as in a column format. In some embodiments a solution of, or isolated compound according to formula (I), or pharmaceutically acceptable salt and/or hydrate thereof, is provided comprising not more than 150 ppm, not more than 50 ppm, not more than 10 ppm metal, not more than 5 ppm, not more than 3 ppm, or not more than 1 ppm metal. In some embodiments, hydrocodone bitartrate or a hydrate thereof produced by the method provided herein comprises not more than 10 ppm, not more than 5 ppm, not more than 3 ppm, not more than 2 ppm, or not more than 1 ppm residual rhodium. In some embodiments, the metal scavenger comprises one or more functional groups selected from the group consisting of acetyl, amide, amine, amino, guanidine, imidazole, imine, mercaptyl, mercaptophenyl, phosphonic acid, trimercaptotriazine, triamine, thiol, or thiourea.

The solvent employed for removal of the transition metal catalyst may be the reaction mixture solution or may be selected from a protic solvent, aprotic solvent or mixtures thereof. In some embodiments, the solvent is selected from water, methanol, ethanol, isopropanol, acetone, methylethyl ketone, or a mixture thereof. In some embodiments, the solvent is a mixture of ethanol and water. In some embodiments, the metal scavenger is employed in a mixture of water and an additional solvent, wherein the pH is an acidic pH selected from a pH within a range of about 0-7, 0-4, 0.5-6, 1-5, 4-7, 2-4, or 4-6. In some embodiments, a pharmaceutically acceptable acid is added to the reaction mixture prior to the treatment with the metal scavenger. In some embodiments, the metal scavenger is employed at a temperature of from about 5-100° C., 10-85° C., 35-60° C., 50-60° C., or ambient temperature. In some embodiments, the reaction mixture or solution comprising the compound of formula (I), or the pharmaceutically acceptable salt thereof is exposed to the metal scavenger for a period of time selected from within about 10 sec to 48 hours, 1 min to 24 h, 5 min to 18 hours, 15 to 90 min, or 40 to 80 min.

In some aspects, the stationary phase metal scavenger is commercially available from Silicycle Inc., Quebec City, Canada or Biotage AB, Uppsala, Sweden. In some aspects, the stationary phase scavenger is selected from BIOTAGE® MP-TMT (polystyrene bound trimercaptotriazine), ISOLUTE® Si-thiol (silica-bound 1-propanethiol), ISOLUTE® Si-TMT (silica bound trimercaptotriazine), ISOLUTE® SCX-2 (silica bound sulfonic acid), or ISOLUTE® Si-trisamine (silica bound propyl-tris(2-aminoethyl)amine). In some embodiments, the metal scavenger is selected from a silica bound thiol (silica bound thiol; e.g. SiliaMetS® Thiol, Si-thiol), thiourea (silica bound thiourea; e.g. SiliaMetS® Thiourea; Si-THU), cysteine (silica bound cysteine; e.g. SiliaMetS® Cysteine, Si-Cys), DMT (silica bound dimercaptotriazine; e.g. SiliaMetS® DMT, Si-DMT), amine (silica bound amine; e.g., SiliaBond® Amine, Si—NH2), imidazole (silica bound imidazole; e.g. SiliaMetS® Imidazole, Si-IMI), TAAcOH (silica bound triaminetetraacetic acid; e.g., SiliaMetS® Triaminetetraacetic acid, Si-TAAcOH), or TAAcONa (silica bound triaminetetraacetate, sodium salt; e.g., SiliaMetS® Tetraacetic acid, sodium salt; Si-TAAcONa) scavenger. In some aspects, the metal scavenger is selected from a silica bound thiol, cysteine, thiourea, or DMT scavenger. In some aspects, the stationary phase metal scavenger is a silica bound thiol.

In some embodiments, a pharmaceutically acceptable acid is added to a reaction mixture comprising a compound of formula (I) and a transition metal catalyst or degradant thereof, the reaction mixture is exposed to a stationary phase metal scavenger, the reaction mixture is filtered to remove the stationary phase metal-scavenger complex, and the pharmaceutically acceptable salt of the compound of formula (I) is allowed to crystallize.

In some specific embodiments, tartaric acid or hydrochloric acid is added to a reaction mixture comprising a compound of formula (I) and a transition metal catalyst or degradant thereof, then the reaction mixture is exposed to a stationary phase metal scavenger for a period of 15 to 90 min at a temperature of from about 20 to 60° C., then the reaction mixture is filtered to remove the stationary phase metal-scavenger complex, and the pharmaceutically acceptable salt of the compound of formula (I) is allowed to crystallize.

In other specific embodiments, the reaction mixture comprising a compound of formula (I) and a transition metal catalyst or degradant thereof is first exposed to a metal scavenger, and then tartaric acid or hydrochloric acid is added to form a pharmaceutically acceptable salt. In some specific embodiments, a stationary phase metal scavenger such as SiliaMetS is added to the reaction mixture comprising a compound of formula (I) and a transition metal catalyst or degradant thereof followed by addition of tartaric acid In one aspect, the isolation procedure is exceptionally simple and provides pure products in high yield. In some embodiments, the compound of formula (I), or pharmaceutically acceptable salt or hydrate thereof, is isolated and/or purified by precipitation, filtration, crystallization, recrystallization, and/or chromatographic purification.

In some embodiments, the compound of formula (I) is isolated in base form in greater than 80%, 85%, or 90% yield, or in the form of a pharmaceutically acceptable salt or solvate thereof in greater than 80% yield.

Recrystallization

In some embodiments, the compound of formula (I) or pharmaceutically acceptable salt thereof is further purified by crystallization and/or recrystallization from an appropriate solvent.

In some embodiments, a method for crystallization and/or recrystallization of the compound of formula (I) or pharmaceutically acceptable salt and/or hydrate thereof is provided by addition of water or water and a combination of one or more organic water miscible solvents, or one or more water miscible solvents. In some embodiments, the one or more organic water miscible solvents are selected from one or more of methanol, ethanol, isopropyl alcohol, methyl ethyl ketone, and acetone. In some embodiments, an appropriate solvent is added to the compound of formula (I) or salt thereof and the mixture is heated to a temperature of from 30 to 100° C., 40 to 80° C., or 50 to 65° C., then allowed to cool.

In some embodiments, the mixture is a solution or slurry. In some embodiments, crystallization is performed by cooling to a temperature between from about 0° C. to about 50° C., between about 10° C. to about 40° C.; from about 15° C. to about 35° C.; or at about ambient temperature.

In some embodiments, crystallization and/or recrystallization of the compound of formula (I) or pharmaceutically acceptable salt or hydrate thereof is provided by a method comprising seed bed crystallization. In some embodiments, a compound of formula (I) or pharmaceutically acceptable salt and/or hydrate thereof is dissolved in one or more organic water miscible solvents selected from one or more of methanol, ethanol, isopropyl alcohol, methyl ethyl ketone, and acetone and the mixture is heated to a temperature above ambient temperature, or from 30 to 100° C., 40 to 80° C., or 50 to 65° C. to form a first mixture solution. In some embodiments, the solution is filtered and the solute is added to a second reactor comprising a second mixture of a compound of formula (I) or pharmaceutically acceptable salt and/or hydrate thereof comprising water and one or more organic water miscible solvents. In some embodiments the second mixture is heated to a temperature above ambient temperature, or from 30 to 100° C., 40 to 80° C., or 50 to 65° C. before adding the first mixture solute. In some embodiments the second mixture remains in the form of a first slurry before adding first mixture solute. In some embodiments the second mixture remains in the form of a slurry throughout the process. In some embodiments, the solute is added to the second mixture over a period of up to 120 minutes, or a period of 1 to 90 minutes, 5 to 60 minutes, or 20 to 40 minutes to form a second slurry and allowed to cool to a temperature of not more than 50° C., not more than 40° C., or not more than 30° C. In some embodiments, the second slurry is cooled to about ambient temperature, or about 20° C., and filtered to obtain the compound of formula (I) or pharmaceutically acceptable salt and/or hydrate thereof. In some embodiments, the second slurry is cooled to improve yield of crystallization.

In some specific embodiments, a method is provided for obtaining isolated crystalline hydrocodone bitartrate or a hydrate thereof by a seed bed crystallization method comprising dissolving hydrocodone base obtained by a method of the disclosure in a water miscible solvent to form a solution, heating the solution to a temperature above ambient temperature or from 30 to 100° C., 40 to 80° C., or 50 to 65° C. and adding about one equivalent of tartaric acid to form a first mixture, filtering the first mixture to obtain a filtrate, adding the filtrate to a second mixture comprising a hydrocodone bitartrate or hydrate thereof in a solvent system comprising water and a water miscible solvent at a temperature above ambient temperature or from 30 to 100° C., 40 to 80° C., or 50 to 65° C. to form a blended mixture, cooling the blended mixture to form a slurry, and filtering the slurry to obtain isolated crystalline hydrocodone bitartrate or a hydrate thereof. In some embodiments, the blended mixture is in the form of a slurry. In some embodiments, the blended mixture is cooled to a temperature of not more than 50° C., not more than 40° C., or not more than 30° C. In some embodiments, the blended mixture is cooled to improve yield of crystallization.

In some embodiments, a method is provided for reducing the amount of residual solvent in an isolated compound of formula (I) or pharmaceutically acceptable salt and/or hydrate thereof comprising exposing to one or more of air, in vacuo, compressed air, humidified compressed air, an inert gas such as argon or nitrogen, or under humidified inert gas, such as humidified nitrogen, to obtain a compound of formula (I) or pharmaceutically acceptable salt and/or hydrate thereof comprising reduced amounts of one or more residual solvents. In some embodiments, a compound of formula (I) or pharmaceutically acceptable salt and/or hydrate thereof is obtained by drying under humidified compressed air, humidified inert gas, such as humidified nitrogen. The humidified compressed air, inert gas, argon or nitrogen may be produced by any method known in the art. In some embodiments, the humidified nitrogen is prepared by passing a stream of nitrogen gas through water or a humidified membrane contactor.

In some embodiments, an isolated compound of formula (I) or pharmaceutically acceptable salt and/or hydrate thereof is provided according to methods of the disclosure having no more than 5000 ppm, or no more than 3000 ppm ethanol. In some embodiments, a compound of formula (I) or pharmaceutically acceptable salt and/or hydrate thereof is provided having no more than 5000 ppm, no more than 3000 ppm, or no more than 2500 ppm acetone. In some embodiments, a compound of formula (I) or pharmaceutically acceptable salt and/or hydrate thereof is provided having no more than 3000 ppm, or no more than 2000 ppm, or no more than 1000 ppm methanol. In some embodiments, a compound of formula (I) or pharmaceutically acceptable salt and/or hydrate thereof is provided having no more than 5000 ppm, or no more than 3000 ppm, or no more than 2000 ppm isopropanol. In some embodiments, a compound of formula (I) or pharmaceutically acceptable salt and/or hydrate thereof is provided having no more than 890 ppm, or no more than 600 ppm, or no more than 500 ppm toluene. In some embodiments, a compound of formula (I) or pharmaceutically acceptable salt and/or hydrate thereof is provided having no more than 370 ppm, or no more than 300 ppm, or no more than 200 ppm cyclooctene. In some embodiments, the compound of formula (I) or pharmaceutically acceptable salt and/or hydrate thereof is hydrocodone bitartrate of a hydrate thereof.

In some specific embodiments, a method is provided for obtaining isolated crystalline hydrocodone bitartrate or a hydrate thereof comprising humidified drying to reduce the amount of residual solvents, for example, wherein the humidified drying comprises exposing hydrocodone bitartrate or a hydrate thereof to a stream of humidified nitrogen to provide hydrocodone bitartrate hemihydrate having not more than 5000 ppm, not more than 4000 ppm, or not more than 3000 ppm of a residual solvent, optionally wherein the residual solvent is selected from ethanol, acetone, methanol, isopropanol.

In some embodiments, a compound of formula (I) or pharmaceutically acceptable salt and/or hydrate thereof is provided according to methods of the disclosure having reduced amounts of impurities and degradants when analyzed by HPLC. In some embodiments, hydrocodone bitartrate or a hydrate thereof is provided having no more than 0.15%, no more than 0.1%, or no more than 0.05% codeinone. An exemplary lot of hydrocodone bitartrate hemipentahydrate prepared by the method of example 6 showed the absence of codeinone in product by HPLC with a limit of detection of detection of 0.06% (600 ppm). In some embodiments, hydrocodone bitartrate or a hydrate thereof is provided having no more than 0.15%, no more than 0.1%, or no more than 0.05% hydromorphone. In some embodiments, hydrocodone bitartrate or a hydrate thereof is provided having no more than 0.15%, no more than 0.1%, or no more than 0.05% codeine. An exemplary lot of hydrocodone bitartrate hemipentahydrate prepared according to example 6 exhibited % peak area purity of 99.76% and codeine content of 0.086% (limit NMT 0.15%) by HPLC method 1 in Example 5. In some embodiments, hydrocodone bitartrate or a hydrate thereof is provided having no more than 0.15%, no more than 0.1%, or no more than 0.05% dihydrocodeine. In some embodiments, hydrocodone bitartrate or a hydrate thereof is provided having no more than 0.15%, no more than 0.1%, or no more than 0.05% methylcodeine. In some embodiments, hydrocodone bitartrate or a hydrate thereof is provided having no more than 0.15%, no more than 0.1%, or no more than 0.05% 10-hydroxyhydrocodone. In some embodiments, hydrocodone bitartrate or a hydrate thereof is provided having no more than 0.15%, no more than 0.1%, or no more than 0.05% bihydrocodone. In some embodiments, hydrocodone bitartrate or a hydrate thereof is provided having no more than 0.1% of any single unknown impurity. In some embodiments, hydrocodone bitartrate or a hydrate thereof is provided having no more than 1.0% total impurities by HPLC.

In some embodiments, the purity of the isolated compound of formula (I) or pharmaceutically acceptable salt or solvate thereof is greater than 97%, 98%, 99%, 99.5% or 99.9% by HPLC. In some embodiments, a compound of formula (I) or pharmaceutically acceptable salt and/or hydrate is provided wherein the starting compound of formula (II) is absent, or present as an impurity at not more than 0.1%, 0.05% or 0.02% by HPLC.

EXAMPLES

Example 1A. Preparation of Aminophosphine Precursor

Figure 3:
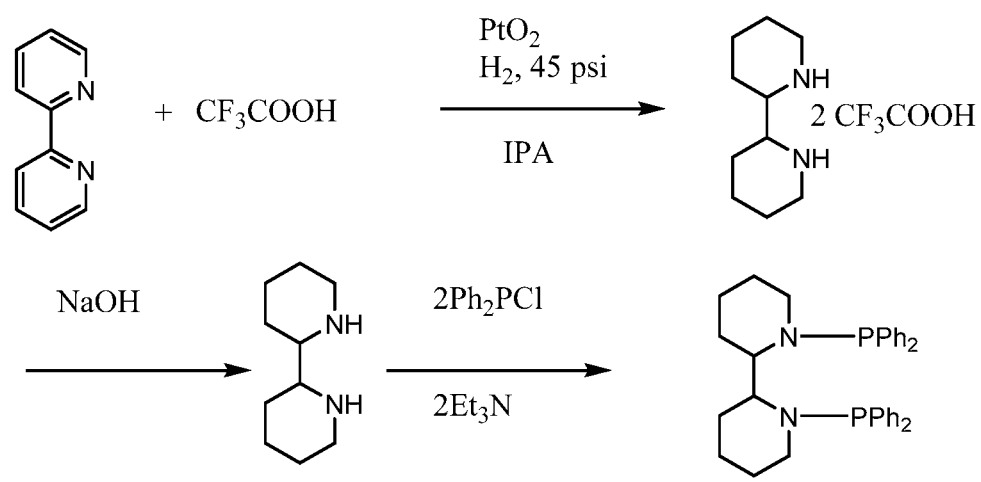
FIG. 3 shows a representative scheme for preparation of an aminophosphine precursor according to formula (IVa) or (IVb).

In this example, aminophosphine precursor 1,1'-bis(diphenylphosphino)-2,2'-bipiperidine was prepared by reducing 1,1'-bipyridyl with PtO$_2$, H$_2$ and TFA to give 1,1'-bispiperidine trifluoroacetate, The TFA salt was converted to 1,1'-bispiperidine free base and treated with diphenylchlorophosphine to obtain aminophosphine precursor 1,1'-bis(diphenylphosphino)-2,2'-bipiperidine, as shown in FIG. 3.

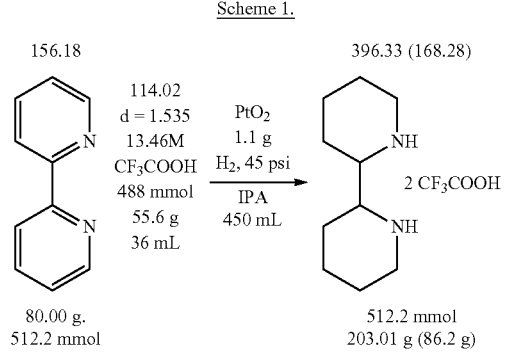 [SMILES: c1ccc(-c2ccccn2)nc1 ; C1CCC(C2CCCCN2)NC1]

Scheme 1.

An 800 mL glass autoclave equipped with magnetic spin bar was charged with 1,1'-bipyridyl (80.00 g, 512.2 mmol) isopropanol (IPA, 450 mL) and trifluoroacetic acid (TFA, 55.6 g, 488 mmol). TFA was added to stirring mixture slowly (over ca 2 min). The mixture was stirred magnetically on air until all solid dissolved (10 min) and then PtO$_2$ (1.1 g) was added. The autoclave was sealed, purged with nitrogen for 10-15 min (through the upper valve using a stainless steel (SS) needle), then with hydrogen and charged with hydrogen to 45 psi. The stirred reaction mixture was heated in oil bath ($t_{bath}$=80° C.) for 90 hours. At this point all Pt catalyst coagulated. The reaction mixture was cooled to room temperature, purged with nitrogen and decanted to 1 L Erlenmeyer flask. Rinse the catalyst inside the autoclave with IPA (50 mL) swirl the mixture, allow the catalyst to settle down and carefully decant the solution in 1 L Erlenmeyer flask. Repeat the wash one more time. The colorless filtrate was treated with TFA (76 g) added upon vigorous stirring in cold water bath, stirred for 1 h and filtered. The filtered solid was washed with IPA (3×200 mL) and dried on air to constant weight to give 1,1'-bispiperidine trifluoroacetate.

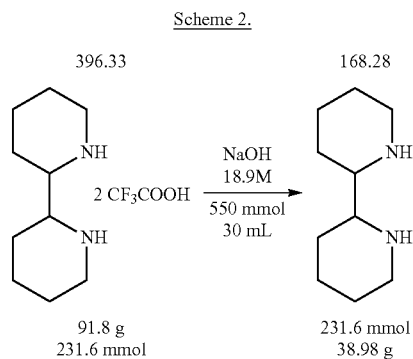 [SMILES: C1CCC(C2CCCCN2)NC1 ; C1CCC(C2CCCCN2)NC1]

Scheme 2.

A stirred slurry of 1,1'-bispiperidine trifluoroacetate in water (150 mL) was treated with 50% NaOH (30 mL) and stirred until all solid dissolved (ca 5 min). The formed solution was extracted three times with dichloromethane (4×90 mL). The combined extracts were stirred with $SiO_2$ (6 g), filtered (filtered $SiO_2$ was washed on filter with extract 4) and evaporated. The obtained oil was dissolved in hexane (150 mL), the resulting slightly turbid solution was dried over NaOH micro pearls (6 g), filtered and evaporated to give 1,1'-bispiperidine free base as colorless oil.

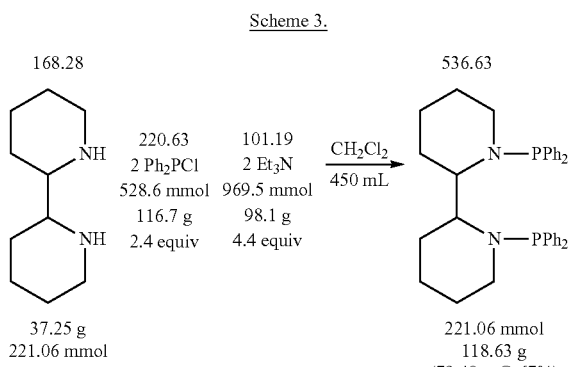

Scheme 3.

The obtained 1,1'-bispiperidine free base was transferred to a nitrogen glove box and dissolved in anhydrous heptane (100 mL). This solution was added drop wise over ca 2.5 hours to a stirred solution of diphenylchlorophosphine (116.7 g, 528.6 mmol) and trimethylamine (98.1 g., 969.5 mmol) in dichloromethane (300 mL). The resulting slurry was stirred magnetically overnight and filtered. The filtered solid was washed with heptane (3×200 mL), removed from the glove box, washed on filter with IPA (150 mL), water (3×250), acetone (150 mL) and dried on air to constant weight to give N,N'-bisdiphenylphosphino-2,2-bipiperidine as a snow-white solid. The aminophosphine precursor 1,1'-bis(diphenylphosphino)-2,2'-bipiperidine was characterized by NMR. $^1$H NMR (300 MHz, $CDCl_3$) δ 7.484-7.279 (m, 20H), 4.05 (d, J=10.5 Hz, 2H), 3.07 (d, J=8.4 Hz, 4H), 2.02 (d, J=9.6 Hz, 2H), 1.601-1.572 (m, 4H), 1.316 (brs, 2H), 1.07 (d, J=12.3 Hz, 2H), 0.583 (m, 2H) ppm. $^{31}$P NMR (121 MHz, $CDCl_3$) δ 66.16 (s) ppm.

Example 1B. In Situ Preparation of the Rh Catalyst and Redox Isomerization of Codeine to Form Hydrocodone or a Pharmaceutically Acceptable Salt or Solvate Thereof In this example, a rhodium aminophosphine complex catalyst is generated in situ and characterized. The catalyst is used for redox isomerization of codeine to form hydrocodone base. Hydrocodone bitartrate salt is prepared without isolation of hydrocodone base.

Preparation of the catalyst was carried out under argon using standard Schlenk technique. Anhydrous toluene was deoxygenated by nitrogen sparging for 1 h. The rhodium-aminophosphine complex catalyst was prepared in situ by adding 2 mL of the oxygen free toluene to chlorobis(cyclooctene) rhodium (1) dimer (17 mg, 0.0236 mmol) and 1,1'-bis(diphenylphosphino)-2,2'-bipiperidine prepared according to Example 1A (25.3 mg, 0.0472 mmol) with agitation, in a 10 mL Schlenk tube under argon blanket. The mixture was stirred for 15 min to give a dark orange solution.

The freshly prepared rhodium-aminophosphine complex catalyst was characterized by $^{31}$P-NMR. $^{31}$P NMR (121 MHz, $C_6D_6$) δ 115 (dd, J=41.3 and 205 Hz, 50H), 90 (dd, J=38.9 and 198 Hz, 50H) ppm. For the oxygenated catalyst: $^{31}$P NMR (121 MHz, $C_6D_6$) δ 26.84 (s) ppm was main oxygenated product. The codeine base monohydrate starting material was characterized by NMR as follows. $^1$H NMR (300 MHz, $CDCl_3$) δ 6.67 (d, J=8.1 Hz, 1H), 6.58 (d, J=8.1 Hz, 11), 5.72 (d, J=9.9 Hz, 11), 5.3 (d, J=9.9 Hz, 11), 4.9 (d, J=6.6 Hz, 11H), 4.19 (brs, 1H), 3.852 (s, 3H), 3.36 (brs, 1H), 3.09-2.95 (m, 2H), 2.68-2.57 (m, 2H), 2.45 (s, 3H), 2.42-2.28 (m, 2H), 2.26-2.11 (m, 1H), 2.07 (brd, J=4.8 Hz, 1H) ppm. $^{13}$C NMR (75 MHz, $CDCl_3$) δ 146.29, 142.20, 133.41, 131.08, 128.31, 127.23, 119.54, 112.84, 91.36, 66.42, 58.88, 56.32, 46.45, 43.14, 42.97, 40.83, 35.86, 20.39 ppm. $^{13}$C NMR DEPT135 (75 MHz, $CDCl_3$) 3 $CH_2$ peaks pointing down δ 46.46, 35.86, 20.39 ppm. 10 CH and $CH_3$ peaks pointing up δ 133.41, 128.31, 119.54, 112.84, 91.36, 66.42, 58.88, 56.32, 43.15, 40.83 ppm. The five quaternary C do not appear in DEPT135 NMR.

A 100 mL round bottom Schlenk flask equipped with return condenser and argon inlet was charged with 50 mL methanol, 2 mL water and codeine base monohydrate (Lot#265-54, 10.00 g, 31.51 mmol).

The mixture was stirred and heated to reflux under argon. Codeine-methanol-water solution was deoxygenated by boiling for 1 h and then the toluene-catalyst solution was added (Concentration of the prepared in situ Rh-catalyst was 0.15 mol % relative to codeine) under oxygen free conditions. Codeine isomerization was monitored by HPLC. The resulting reaction mixture was stirred and refluxed under argon for 1.75 h. After 0.75 h of reaction time, hydrocodone base crystallization was observed. At 1.75 h codeine conversion was 99.92% by HPLC. The resulting slurry was diluted with methanol (10 mL) and treated with a tartaric acid water solution (2.36 g tartaric acid (15.72 mmol) in 30 mL water) containing 0.5 equivalents of tartaric acid relative to the theoretical hydrocodone base concentration. Total dissolution was observed immediately and the homogeneous hydrocodone tartrate clear solution was transferred to a 500 mL round bottom flask equipped with return condenser.

Acetone (70 mL) was used to clean the 100 mL Schlenk and tartaric acid vial. All washes were added to the hydrocodone tartrate solution. The magnetically stirred mixture was heated to reflux, diluted with an additional 70 mL of the acetone and treated with the second portion of the tartaric acid (2.83 g., 18.86 mmol, 0.6 eq.) in water (7 mL)/acetone (20 mL) mixture. Acetone (45 mL) was added to hydrocodone bitartrate boiling solution. Solution was cooled down and precipitation was started after 10 min of the cooling. When crystallization started, acetone (70 mL) was added to the slurry. Additional amount of the acetone (140 mL) was slowly added to the slurry in two portions (2×70 mL) during the precipitation. The stirring was stopped. Acetone (40 mL) was added to the slurry and a spatula was used to continue stirring. The mixture was heated to 58° C., refluxed 10 min and slurry was cooled to room temperature overnight. The resulting slurry was filtered; the solids were washed with acetone (3×150 mL) and hexanes (2×100 mL) and dried on an air to constant weight to give hydrocodone bitartrate hemipentahydrate as a snow white solid. The hydrocodone bitartrate hemipentahydrate corresponds to a compound of formula I wherein $R_1$ is $CH_3$, $R_2$ is $CH_3$, and $R_3$ is H. The yield of hydrocodone bitartrate hemipentahydrate was 14.35 g., 92.1%. Hydrocodone bitartrate hemipentahydrate HPLC purity was 99.93%. Codeine content was 0.01% (limit NMT 0.15%).

Samples were tested for loss on drying (LOD) according to USP monograph. Additionally, data showing the XRPD diffractogram of material was found to correspond to the USP reference standard for the hemipentahydrate (data not shown).

The hydrocodone bitartrate hemipentahydrate was characterized by NMR.

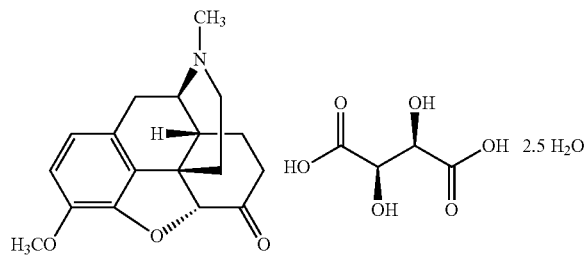

$^1$H NMR (300 MHz, $D_2O$) δ 6.68 (dd, J=8.4 and 16.5 Hz, 2H), 5.044 (s, 1H), 4.416 (s, 2H), 3.96 (brs, 1H), 3.789 (s, 3H), 3.242-3.070 (m, 3H), 2.867 (s, 3H), 2.834-2.694 (m, 2H), 2.631-2.536 (m, 1H), 2.324-2.279 (m, 2H), 1.931-1.887 (m, 2H), 1.122-1.074 (m, 1H) ppm.

$^{13}$C NMR (75 MHz, $D_2O$) δ 211.95, 176.33, 144.48, 142.58, 125.24, 123.60, 121.26, 115.35, 90.57, 72.79, 61.00, 56.66, 47.61, 45.23, 40.70, 39.48, 38.73, 32.45, 24.49, 20.13 ppm.

$^{13}$C NMR DEPT135 (75 MHz, $CDCl_3$) 5 $CH_2$ peaks pointing down δ 47.61, 38.73, 32.45, 24.49, 20.13 ppm. 8 CH and $CH_3$ peaks pointing up δ 121.26, 115.35, 90.57, 72.79, 61.00, 56.66, 40.70, 39.48 ppm. The seven quarternary C do not appear in DEPT135 NMR 7 peaks.

Example 2. In Situ Preparation of the Rh Catalyst and Redox Isomerization of CPS-C to Hydrocodone Bitartrate Hemipentahydrate In this example, a rhodium aminophosphine complex catalyst is generated in situ and used for redox isomerization of concentrated poppy straw-codeine (CPS-C) to form hydrocodone base. Hydrocodone bitartrate salt is prepared without isolation of hydrocodone base.

Preparation of the catalyst was carried out under nitrogen using standard Schlenk technique. Anhydrous toluene was deoxygenated by nitrogen sparging for 1 h. The rhodium-aminophosphine complex catalyst was prepared in situ by adding 2 mL of the oxygen free toluene to chlorobis(cyclooctene) rhodium (1) dimer (8.5 mg, 0.0118 mmol) and 1,1'-bis(diphenylphosphino)-2,2'-bipiperidine (12.7 mg, 0.0236 mmol) with agitation, in a 10 mL Schlenk tube in nitrogen atmosphere. The mixture was stirred for 15 min to give a dark orange solution.

A new 250 mL round bottom Schlenk flask equipped with return condenser and nitrogen inlet was charged with 67 mL denatured ethanol (95% alcohol) and Concentrated Poppy Straw-Codeine (CPS-C) (11.00 g, 10.00 codeine based on 9.06% LOD, 33.4 mmol). The mixture was stirred magnetically and heated to reflux under nitrogen. Codeine-ethanol solution was deoxygenated by boiling for 1 h and then the toluene-catalyst solution was added (concentration of the prepared in situ Rh-catalyst was 0.07 mol % relative to codeine) under oxygen free conditions. Codeine isomerization was monitored by HPLC. The resulting reaction mixture was stirred and refluxed under nitrogen for 6 h. Hydrocodone base crystallization was not observed during codeine isomerization. At 6 h codeine conversion was 99.84%.

The resulting slurry was cooled to 55° C. and treated with a tartaric acid water solution (2.36 g tartaric acid, 15.72 mmol, in 6 mL water) containing 0.47 equivalents of tartaric acid relative to the theoretical hydrocodone base concentration. Total dissolution was observed immediately and the homogeneous hydrocodone tartrate clear solution was treated with 0.5 g. of the SiliaMetS (Loading: 0.52 mmol/g, 5% relative to codeine). Slurry was stirred 1 h and then SiliaMetS was filtered off through fine porosity filter. Filtrate was transferred to a preheated (55° C.) 250 mL jacked reactor equipped with mechanical stirrer and return condenser. Denatured ethanol (21 mL) and water (6 mL) were using to clean 250 mL Schlenk, SiliaMetS cake on the filter, filtrate flask and tartaric acid vial. All washes were added to the hydrocodone tartrate solution. The mixture was treated with the second portion of the tartaric acid (2.83 g., 18.86 mmol, 0.57 eq.) in water (6 mL). Tartaric acid vial was washed with denatured ethanol (5 mL). The total amount of the solvents was 111 mL—denatured ethanol 93 mL and water 18 mL. The resulting dark brown solution was stirred at 55° C. for 2 h to allow for crystallization. After 0.5 h, significant crystallization of the hydrocodone bitartrate was observed. The resulting slurry was cooled down to room temperature, stirred at this temperature for 1 h, and filtered. The filtered solid was washed with denatured ethanol (3×75 mL) and hexanes (2×125 mL) and dried on an air to constant weight to give hydrocodone bitartrate hemipentahydrate as a snow white solid. The yield was 14.61 g., 88.4%. Hydrocodone bitartrate hemipentahydrate HPLC purity was 99.85%. Codeine content was 0.014% (limit NMT 0.15%). Characterization by NMR was performed.

Example 3. In Situ Preparation of the Rh Catalyst and Redox Isomerization of 14-Hydroxycodeine to Oxycodone Preparation of the catalyst was carried out under nitrogen using standard Schlenk technique. Anhydrous toluene was deoxygenated by nitrogen sparging for 1 h. The rhodium-aminophosphine complex catalyst was prepared in situ by adding 2 mL of the oxygen free toluene to chlorobis(cyclooctene) rhodium (1) dimer (8.5 mg, 0.0119 mmol) and 1,1'-bis(diphenylphosphino)-2,2'-bipiperidine (12.8 mg, 0.0238 mmol) with agitation, in a 10 mL Schlenk tube under nitrogen blanket. The mixture was stirred for 15 min to give a dark orange solution.

A new 100 mL round bottom Schlenk flask equipped with return condenser and gas inlet was charged with 23 mL methanol and 14-hydroxycodeine base (2.5 g, 7.93 mmol). The mixture was stirred magnetically and heated to reflux under nitrogen for 1 h and then the toluene-catalyst solution was added (concentration of the prepared in situ Rh-catalyst was 0.15 mol % relative to 14-hydroxycodeine) under oxygen free conditions. 14-Hydroxycodeine isomerization was monitored by HPLC. The resulting reaction mixture was stirred and refluxed under nitrogen for total of 23 hrs. After 55 mins, conversion of 14-hydroxycodeine to oxycodone was 15.5% based on HPLC analysis. After 5 h of reaction, 14-hydroxycodeine conversion was 58.8%. The reaction was left overnight and tested the next day (total 23 h) where 97.82% conversion was observed. At that time reaction mixture was cooled to 0 to 5° C. Crystallization was observed instantly. The resulting slurry was stirred at 0 to 5° C. for another hour followed by filtration; the solids were washed with cold methanol (2×8 mL) and dried to constant weight to give oxycodone base. The oxycodone base corresponds to a compound of formula I wherein $R_1$ is $CH_3$, $R_2$ is $CH_3$, and $R_3$ is OH. The yield was 2.06 g, 82.4%. Purity was 99.55% based on HPLC analysis.

The oxycodone base was characterized by NMR.

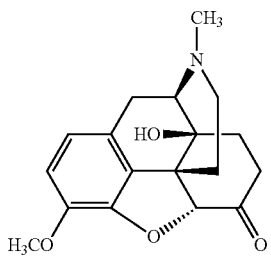 [SMILES: COc1ccc2c3c1O[C@H]1C(=O)CC[C@@]4(O)[C@@H](C2)N(C)CC[C@]314]

$^1$H NMR (300 MHz, CDCl$_3$) d 6.67 (br d, 15 Hz, 2H), 5.067 (s, 1H), 4.662 (s, 1H), 3.901 (s, 3H), 3.190-3.023 (m, 2H), 2.861 (s, 1H), 2.592-2.321 (m, 2H), 2.408 (s, 3H), 2.321-2.167 (m, 3H), 1.851 (m, 1H), 1.628-1.584 (m, 2H) ppm.

$^{13}$C-NMR (75 MHz, CDCl$_3$) δ 208.51, 145.01, 142.97, 129.39, 124.94, 119.42, 114.91, 90.39, 70.36, 64.59, 56.83, 50.24, 45.24, 42.73, 36.13, 31.42, 30.52, 21.91 ppm. $^{13}$C NMR DEPT135 (75 MHz, CDCl$_3$) 5 CH$_2$ peaks pointing down δ 45.24, 36.14, 31.43, 30.53, 21.91 ppm; 6 CH and CH$_3$ peaks pointing up δ 119.42, 114.91, 90.39, 64.59, 56.84, 42.73 ppm. The quaternary Cs do not appear in DEPT135 (7 peaks).

Example 4. In Situ Preparation of the Rh Catalyst and Redox Isomerization of Morphine Base to Hydromorphone Base Preparation of the catalyst was carried out under nitrogen blanket. Anhydrous toluene was deoxygenated by nitrogen sparging for 1 h. The rhodium-aminophosphine complex catalyst was prepared in situ by adding 3.8 mL of the oxygen free toluene to chlorobis(cyclooctene) rhodium (1) dimer (47 mg, 0.066 mmol) and 1,1'-bis(diphenylphosphino)-2,2'-bipiperidine (70.5 mg, 0.13 mmol) with agitation, in a 10 mL Schlenk tube under nitrogen blanket. The mixture was stirred to give a dark orange solution.

A new 500 mL round bottom Schlenk flask equipped with return condenser and gas inlet was charged with 150 mL methanol, Morphine base monohydrate (26.6 g, 0.088 mol) and Sodium Methoxide (3.58 g, 0.066). The mixture was stirred mechanically at 150 rpm and heated to reflux under nitrogen for at least 30 min then cooled to 5-15° C. below boiling point and then the toluene-catalyst solution was added under oxygen free conditions. The mixture was then heated to reflux temp and held at reflux temp while monitoring reaction completion. Morphine base isomerization to Hydromorphone base was monitored by HPLC. The resulting reaction mixture was stirred and refluxed under nitrogen for a total of 18 hrs, at which time conversion of Morphine base to Hydromorphone was 99% based on HPLC analysis. At that time reaction volume was distilled to approximately 80 mL. Glacial acetic acid was then added to reaction mixture over 15 min to a pH of 9.3. The reaction mixture was then cooled to 10° C. and allowed to mix and crystallize for 15 min. Final slurry was filtered and washed with IPA (3×, 50 ml) to provide hydromorphone base. Hydromorphone base corresponds to a compound of formula I wherein $R_1$=H, $R_2$=CH$_3$, and $R_3$=H. The yield of hydromorphone base was 22.4 g, 89.4%. HPLC purity: Hydromorphone=99.24%.

The hydromorphone base was characterized by NMR.

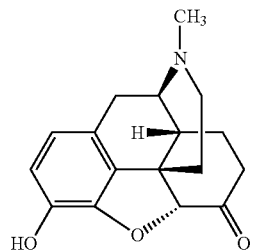 [SMILES: CN1CC[C@]23c4c5ccc(O)c4O[C@H]2C(=O)CC[C@H]3[C@H]1C5]

$^1$H NMR (300 MHz, DMSO) δ 9.14 (s, 1H), 6.553-6.486 (dd, 2H), 4.817 (s, 1H), 3.07 (bs, 1H), 3.85-2.91 (d, 1H), 2.50-253 (m, 4H), 2.41-2.44 (d, 1H), 2.236 (s, 3H), 2.221-2.24 (4, 2H), 2.21 (m, 2H), 1.75 (m, 1H), 1.5 (m, 1H), 1.00 (dd 1H) ppm. DMSO (NMR solvent) residual signal appear as a multiplet at 2.5 ppm which overlaps with the resonances of the protons of hydromorphone. The signal at δ 3.3 belongs to residual water in DMSO-d6.

$^{13}$C-NMR (75 MHz, DMSO) δ 209.30, 144.36, 139.66, 127.87, 124.96, 119.67, 117.29, 90.82, 58.71, 46.80, 46.65, 43.01, 41.95, 40.14, 35.30, 25.45, 19.92 ppm. $^{13}$C NMR DEPT135 (75 MHz, DMSO) 5 CH$_2$ peaks pointing down δ 46.80, 40.13, 35.30, 25.45, 19.92 ppm; 6 CH and CH$_3$ peaks pointing up δ 119.67, 117.29, 90.82, 58.71, 43.01, 41.95 ppm. The quaternary Cs do not appear in DEPT135 (6 peaks).

Example 5. HPLC Methods

Methods are provided for the production of compounds of formula (I) with the goal of minimizing one or more process impurities. The presence and quantification of process impurities in starting materials, intermediates and final product was detected by HPLC and associated methods. Generally, reverse phase HPLC was employed for detection and quantification of impurities. Various HPLC methods were employed.

HPLC Method 1: Analytical Reverse-Phase (RP)—High Pressure Liquid Chromatography (RP-HPLC) of the final product and intermediates disclosed herein was performed under the following conditions. RP-HPLC was performed using a C18 stationary phase with an Agilent Poroshell 120 EC-C18, 2.7 μm, LC Column 100×4.6 mm, Part: 695975-902. The method was run under gradient HPLC Conditions: Mobile phase A: 95:5 Ion pairing buffer:ACN; Mobile phase B: ACN, at a Flow rate of 1.5 mL/min, at 50° C., and with monitoring at 280 nm. Gradient with cure (6), 0 mins-16% B, 20 mins-16% B, 23 mins-40% B, 25 mins-40% B, 25.1 mins-16% B, and 31 mins-16% B. Injection 5 to 50 uls. Preparation of RP HPLC buffer was as follows.

Dissolve 1.5 g of 1-Decane Sulfonic Acid, Sodium Salt and 0.7 g of Sodium phosphate monobasic anhydrous into 1000 mL of water. Adjust the pH to 3.0±0.05 with phosphoric acid and filter.

Combine 950 mL of buffer with 50 mL acetonitrile and mix well.

HPLC method 2: RP-HPLC was performed using a Phenomenex Luna C-18(2) column, 3.0 μm, 75×4.6 mm, Part: OOC-4251-EO. The method was run under gradient HPLC Conditions: Mobile phase A: 90:10 Ion pairing buffer: MeOH; Mobile phase B:MeOH, at a Flow rate of 1.8 mL/min, at 40° C., and with monitoring at 210 nm. Gradient with curve 6 up to 9 mins and curve 11 up to 11 mins, 0 mins-20% B, 2 mins-20% B, 7 mins-60% B, 9 mins-70% B, 10 mins-20% B, and 11 mins-20% B. Injection 5 to 50 uls. Preparation of RP HPLC buffer was as follows.

Dissolve 3.0 g of Octane Sulfonic Acid, Sodium Salt into 900 mL of water. Add 100 mL MeOH and 0.2 mL phosphoric acid, mix well and filter.

HPLC Method 3: Analytical Reverse-Phase (RP)—High Pressure Liquid Chromatography (RP-HPLC) of the final product and intermediates disclosed herein was performed under the following conditions. RP-HPLC was performed using a C18 stationary phase with a Gemini® 3 m C18 110 Å, LC Column 150×4.6 mm, Part: 00F-4453-EO. The method was run under HPLC Conditions: Mobile phase at a Flow rate of 1 mL/min, at 40° C., and with monitoring at 300 nm. Preparation of RP HPLC buffer was as follows.

A: Dissolve 6.9 g of $NaH_2PO_4 \times H_2O$ in 2000 mL of water. Add 10.8 g of Dodecyl Sulfate, Sodium Salt and mix until well dissolved. Filter. Adjust the pH to 7.9 with triethylamine.

B: Combine 1460 mL of buffer with 300 mL acetonitrile and 240 mL of methanol and mix well. Adjust the apparent pH of mobile phase to a target range of 8.8 with 50% aqueous sodium hydroxide or 85% aqueous phosphoric acid solution.

Example 6. In Situ Preparation of the Rh Catalyst and Redox Isomerization of CPS-C to Hydrocodone Bitartrate Hemipentahydrate with Crystallization Utilizing Seed Bed Transfer Preparation of the catalyst was carried out under nitrogen using standard Schlenk technique. Anhydrous toluene was deoxygenated by nitrogen sparging for 20 min. The rhodium-aminophosphine catalyst was prepared in situ by adding 3 mL of the oxygen free toluene to chlorobis(cyclooctene) rhodium (1) dimer (17 mg, 0.0236 mmol) and 1,1'-bis(diphenylphosphino)-2,2'-bipiperidine (25.3 mg, 0.0472 mmol) with agitation, in a 10 mL Schlenk tube under nitrogen blanket. The mixture was stirred for 15 min to give a dark orange solution.

A new 400 mL EasyMax™ reactor (Mettler-Toledo AG, Schwerzenbach, Switzerland) equipped with mechanical stirrer and return condenser and nitrogen inlet was charged with 164.6 mL denatured ethanol (90% ethanol, 5% methanol, 5% IPA), 43.9 mL acetone, and Concentrated Poppy Straw-Codeine (CPS-C) (25.00 g, 22.00 codeine based on 12% LOD, 73.49 mmol). The mixture was stirred and heated to reflux under nitrogen. The codeine-denatured ethanol-acetone solution was deoxygenated by boiling for 30 min and then the toluene-catalyst solution was added (Concentration of the prepared in situ Rh-catalyst was 0.15 mol % relative to codeine) under oxygen free conditions. Codeine isomerization was monitored by HPLC. The resulting reaction mixture was stirred and refluxed under argon for 4 h. After 2 h of reaction time, hydrocodone base crystallization was observed. At 4 h codeine conversion was 99.77%. The resulting slurry was cooled to 65° C. and diluted with acetone (43.9 mL). Total dissolution of the precipitated hydrocodone was observed immediately and the homogeneous hydrocodone base solution was treated with 2.2 g of SiliaMetS® Thiol silica gel (loading: 0.52 mmol/g, 10% relative to codeine). The slurry was stirred at 65° C. for 2 hours and then the SiliaMetS was filtered off through a medium porosity filter to provide a hydrocodone filtrate. The hydrocodone filtrate was subjected to seed bed crystallization as follows in order to avoid crash crystallization and improve crystalline product quality.

The hydrocodone filtrate was transferred to a new 400 mL EasyMax™ reactor equipped with mechanical stirrer and return condenser. This solution was heated to 65° C. and treated with tartaric acid (12.13 g, 80.84 mmol, 1.1 molar equivalents relative to the theoretical hydrocodone base). This hydrocodone bitartrate solution was kept at 65° C. to keep the solution above its solubility point. A second 400 mL EasyMax™ reactor equipped with mechanical stirring and return condenser was charged with hydrocodone bitartrate hemipentahydrate (7.2 g), water (8.1 mL), denatured ethanol (29 mL), and acetone (15.7 mL). This second reactor was heated to 50° C. to maintain a warm slurry of hydrocodone bitartrate. The hydrocodone bitartrate solution in the first reactor was transferred to the second reactor over 30 minutes by using pressurized nitrogen. Once the transfer was finished, complete, fluid crystallization was observed. The slurry was then cooled to 20° C. and filtered once temperature was met. The filtered solid was washed with acetone (2×75 mL) and dried on an air to constant weight to give hydrocodone bitartrate hemipentahydrate as a snow white solid. The yield was 31.52 g, 87.2%. Hydrocodone bitartrate hemipentahydrate purity was 99.76% by HPLC method 1 of Example 5. Codeine content was 0.086% (limit NMT 0.15%). Specific rotation for product produced by this method per USP 781S is between −79° and −84°.

Example 7. Drying of Hydrocodone Bitartrate Hemipentahydrate Using Humidified Nitrogen to Displace Residual Solvents A method involving humidified drying to reduce residual solvents in hydrocodone bitartrate hemipentahydrate was performed. Room temperature water was charged into a 3 neck round bottom flask. A double walled condenser was installed into the middle neck and a temperature controller (Julabo) was connected and set to 80° C. Rubber septums were used to plug the two side necks of the flask. The nitrogen supply line was connected to a rotameter to accurately measure and control the flowrate at 2.3 L/min. This nitrogen line was then connected to a needle and put through the septum into the water. The flow path for the nitrogen was through the water, then through the heat exchanger, and then to the bottom outlet of a 500 mL reactor containing 25 g of hydrocodone bitartrate powder containing 1.35% and 1.15% ethanol and acetone respectively. The nitrogen was observed to be exiting the heat exchanger at ~40° C. The nitrogen was allowed to flow through the product and vent through the top of the reactor. Samples were taken at 0, 2, 24, and 29 hours. The residual solvents were observed to drop over each sample time. After 29 hours of flowing humidified nitrogen through the product the ethanol and acetone were tested and found to be 2913 ppm (0.29%) an 1132 ppm (0.11%) respectively. Passing specifications requires these residual solvents be below 5000 ppm each.

Example 8. Analysis of Hydrocodone Bitartrate Hemipentahydrate for Rh

Hydrocodone bitartrate hemihydrate product produced by the method of examples 6 and 7 was subjected to analysis for residual rhodium (Rh). The sample was dissolved in a solution containing 1% nitric acid, 3% hydrochloric acid and internal standards. Sample solutions were analyzed using an Agilent 7500 Inductively Coupled Plasma Mass Spectrometer (ICP-MS) in the He collision mode. Hydrocodone bitartrate hemihydrate product exhibited not more than 10 ppm residual Rh in order to pass internal specifications. Two exemplary lots exhibited 0.29 ppm and 0.31 ppm Rh, respectively.

Example 9. Pressurized Reaction

Preparation of the catalyst was carried out using standard Schlenk technique. Anhydrous toluene was deoxygenated by nitrogen sparging for 30 min. The rhodium-aminophosphine catalyst was prepared in situ by adding 2 L of the oxygen free toluene to chlorobis(cyclooctene) rhodium (1) dimer (19.9 g, 25.6 mmol) and 1,1'-bis(diphenylphosphino)-2,2'-bipiperidine (29.8 g, 55.5 mmol) with agitation, in a 6 L three neck flask under nitrogen blanket. The mixture was stirred for 15 min to give a dark orange solution.

A 200 L Hastelloy® reactor equipped with mechanical stirrer, return condensor, and nitrogen inlet was charged with 68.8 kg denatured ethanol (95% ethanol, 5% methanol, 5% IPA), 18.3 kg acetone, and Concentrated Poppy Straw-Codeine (CPS-C) (13.2 kg, 11.6 kg codeine based on 12% LOD, 38.8 mol). The mixture was stirred and heated to reflux under nitrogen. Codeine-denatured ethanol-acetone solution was deoxygenated by boiling for 30 min and then the toluene-catalyst solution was added (concentration of the prepared in situ Rh catalyst was 0.15 mol % relative to codeine) under oxygen free conditions and set the reactor pressure to 10 PSIG. Codeine isomerization was monitored by HPLC. The resulting reaction mixture was stirred and refluxed under nitrogen for 4 h. At 2.5 h codeine conversion was 99.5%.

We claim:
1. A method of preparing a compound of formula (I) or a pharmaceutically acceptable salt and/or solvate thereof

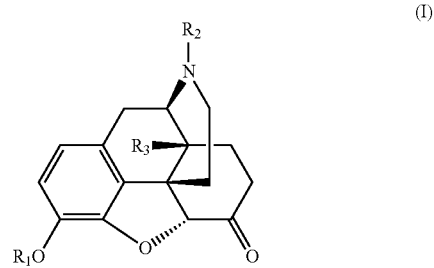

(I)

wherein
$R_1$ is selected from H, or optionally substituted $C_{1-18}$ alkyl, $C_{2-18}$ alkenyl, $C_{2-18}$ alkynyl, or $C_{3-18}$ cycloalkyl, or $R^P$, wherein $R^P$ is a hydroxy protecting group;
$R_2$ is selected from H, or optionally substituted $C_{1-18}$ alkyl, $C_{2-18}$ alkenyl, $C_{2-18}$ alkynyl, or $C_{3-18}$ cycloalkyl, or $R^Q$, wherein $R^Q$ is a nitrogen protecting group; and
$R_3$ is selected from H, —OH, or optionally substituted $C_{1-18}$ alkyl, $C_{1-18}$ alkoxy, $C_{2-18}$ alkenyl, $C_{2-8}$ alkynyl, or $C_{3-18}$ cycloalkyl, or —$OR^P$, wherein $R^P$ is a hydroxy protecting group, the method comprising
exposing a compound of formula (II)

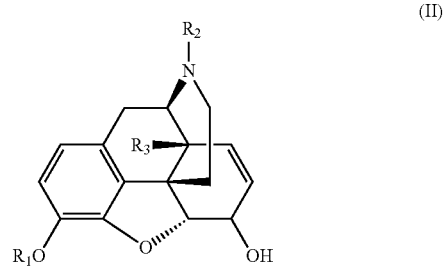

(II)

wherein $R^1$, $R^2$ and $R^3$ are as defined above,
to a transition metal complex catalyst of formula (III)

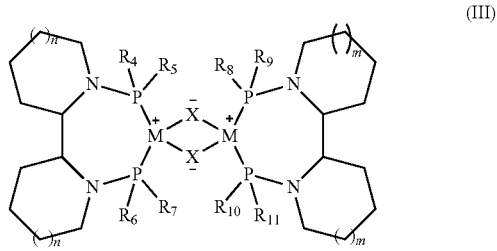

(III)

wherein
M is selected from Rh or Ir;
each X is independently H, —OH, halo, alkoxy, aryloxide, an anion or a solvent molecule;
$R_4$, $R_5$, $R_6$, $R_7$, $R_8$, $R_9$, $R_{10}$ and $R_{11}$ are independently selected from H and optionally substituted aryl, heterocyclic, or cycloalkyl;
n is 0 or 1; and
m is 0 or 1.

2. The method of claim 1, wherein $R_1$ is H or $C_{1-6}$ alkyl; $R_2$ is H, $C_{1-6}$ alkyl, $C_{2-6}$ alkenyl, or $C_{3-6}$ cycloalkyl; and $R_3$ is H, or —OH.

3. The method of claim 2, wherein $R_1$ is H or $CH_3$; $R_2$ is $CH_3$, allyl, or cyclopropylmethyl; and $R_3$ is H or —OH.

4. The method of claim 3, wherein $R_1$ is H or $CH_3$; $R_2$ is $CH_3$; and $R_3$ is H or OH.

5. The method of claim 4, wherein $R_1$ is H or $CH_3$; $R_2$ is $CH_3$; and $R_3$ is H.

6. The method of claim 5, wherein $R_1$ is H; $R_2$ is $CH_3$; and $R_3$ is H.

7. The method of claim 5, wherein $R_1$ is $CH_3$; $R_2$ is $CH_3$; and $R_3$ is H.

8. The method of claim 7, wherein the compound of formula (II) is codeine base or a hydrate thereof or concentrated poppy straw-codeine (CPS-C).

9. The method of claim 1, wherein X is halo; and $R_4$, $R_5$, $R_6$, $R_7$, $R_8$, $R_9$, $R_{10}$ and $R_{11}$ are each optionally substituted aryl.

10. The method of claim 9, wherein M is Rh; $R_4$, $R_5$, $R_6$, $R_7$, $R_8$, $R_9$, $R_{10}$ and $R_{11}$ are each phenyl; m is 1; and n is 1.

11. The method of claim 1, wherein the exposing comprises adding 0.05-0.3 mol % of the compound of formula (III) to the compound of formula (II), to transform the compound of formula (II) into the compound of formula (I) or salt or solvate thereof.

12. The method of claim 11, wherein the transformation of compound (II) into the compound of formula (I) is greater than 97%, 99%, 99.5%, or 99.9% by HPLC.

13. The method of claim 1, further comprising dissolving the compound of formula (II) in a solvent selected from the group consisting of methanol, ethanol, isopropanol, n-propanol, water, methylene chloride/methanol, tetrahydrofuran, and acetone prior to the exposing step.

14. The method of claim 1, further comprising adding a pharmaceutically acceptable acid to the compound of formula (I) to form the pharmaceutically acceptable salt of the compound of formula (I) or the solvate thereof.

15. The method of claim 14, wherein the pharmaceutically acceptable acid is added to the base form of the compound of formula (I) without isolating the base form.

16. The method of claim 14, wherein the pharmaceutically acceptable acid is an inorganic acid selected from the group consisting of hydrochloric acid, hydrobromic acid, sulfuric acid, nitric acid, and phosphoric acid; or an organic acid selected from the group consisting of acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid.

17. The method of claim 14, further comprising isolating the pharmaceutically acceptable salt of the compound of formula (I) or the solvate thereof by crystallization.

18. The method of claim 17, wherein the pharmaceutically acceptable salt of the compound of formula (I) or the solvate thereof is isolated in greater than 80% yield compared to the compound of formula (II).

19. The method of claim 18, wherein the purity of the isolated pharmaceutically acceptable salt of the compound of formula (I) or the solvate thereof is greater than 99%.

20. A method of catalytically converting codeine into hydrocodone or morphine into hydromorphone comprising exposing the codeine or morphine to at least one transition metal aminophosphine complex catalyst of formula (III)

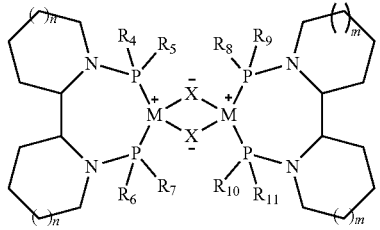

wherein

M is selected from Rh or Ir;

each X is independently H, —OH, halo, alkoxy, aryloxide, an anion or a solvent molecule;

$R_4$, $R_5$, $R_6$, $R_7$, $R_8$, $R_9$, $R_{10}$ and $R_{11}$ are independently selected from H and optionally substituted aryl, heterocyclic, or cycloalkyl;

n is 0 or 1; and m is 0 or 1.

21. The method of claim 20, wherein 0.05-0.3 mol % of the at least one transition metal aminophosphine complex catalyst of formula (III) is added to the codeine or morphine to form a reaction mixture.

22. The method of claim 20, further comprising dissolving the morphine or codeine in a solvent selected from the group consisting of water, methanol, ethanol, isopropanol, n-propanol, methylene chloride/methanol, tetrahydrofuran, and acetone prior to the exposing step.

23. The method of claim 21, wherein the reaction mixture is heated to a temperature selected from 35° C. to 100° C.

24. The method of claim 23, wherein the reaction mixture is heated for a period of 0.5 to 48 hours.

25. The method of claim 24, wherein the transformation of codeine into hydrocodone or morphine into hydromorphone is greater than 97% by HPLC.

26. The method of claim 20, further comprising generating the at least one transition metal aminophosphine complex catalyst of formula (III) in situ by mixing an aminophosphine of formula (IVa) and/or (IVb)

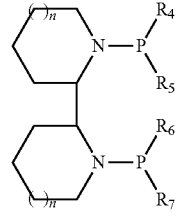

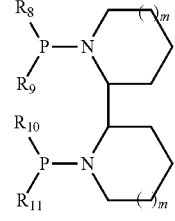

in a solvent with a transition metal precursor of formula (V)

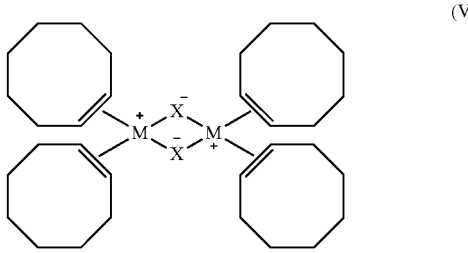

wherein
M is selected from Rh or Ir;
each X is independently H, —OH, halo, alkoxy, aryloxide, an anion or a solvent molecule;
$R_4$, $R_8$, $R_6$, $R_7$, $R_8$, $R_9$, $R_{10}$ and $R_{11}$ are independently selected from H and optionally substituted aryl, heterocyclic, or cycloalkyl;
n is 0 or 1; and
m is 0 or 1.

27. The method of claim 26, wherein M is Rh or Ir; X is halo; $R_4$, $R_5$, $R_6$, $R_7$, $R_8$, $R_9$, $R_{10}$ and $R_{11}$ are aryl; n is 1; and m is 1.

28. The method of claim 27, wherein M is Rh; X is Cl; $R_4$, $R_5$, $R_6$, $R_7$, $R_8$, $R_9$, $R_{10}$ and $R_{11}$ are phenyl.

29. The method of claim 26, wherein the solvent is selected from toluene, xylenes, 4-xylene, 3-xylene, 2-xylene, p-cymene, hexane and methylcyclohexane.

30. The method of claim 21, wherein the codeine is concentrated poppy straw-codeine (CPS-C) used without purification.

31. The method of claim 21, further comprising adding a pharmaceutically acceptable acid to the hydrocodone or hydromorphone to form the pharmaceutically acceptable salt of the hydrocodone or hydromorphone or the solvate thereof.

32. The method of claim 31, wherein the pharmaceutically acceptable acid is added to the base form of the hydrocodone or hydromorphone without isolating the base form.

33. The method of claim 32, wherein the pharmaceutically acceptable acid is an inorganic acid selected from the group consisting of hydrochloric acid, hydrobromic acid, sulfuric acid, nitric acid, and phosphoric acid; or an organic acid selected from the group consisting of acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid.

34. The method of claim 33, further comprising isolating the pharmaceutically acceptable salt of the hydrocodone or hydromorphone or the solvate thereof by crystallization.

35. The method of claim 34, wherein the pharmaceutically acceptable salt of the hydrocodone or hydromorphone or the solvate thereof is isolated in greater than 80% yield compared to the codeine or morphine.

36. The method of claim 35, wherein the purity of the isolated pharmaceutically acceptable salt of the hydrocodone or hydromorphone or the solvate thereof is greater than 99%.

37. The method of claim 25, wherein the reaction mixture is heated under increased pressure in a reactor for a period of about 0.5 to about 4 hours.

38. The method of claim 34, wherein the pharmaceutically acceptable salt of the hydrocodone or hydromorphone or the solvate thereof is prepared by a method comprising seed bed crystallization.

39. The method of claim 38, wherein the seed bed crystallization comprises
dissolving or diluting the base form of the compound of hydrocodone or hydromorphone in a water miscible solvent;
adding the pharmaceutically acceptable acid to form a solution;
mixing the solution with a first slurry of a pharmaceutically acceptable salt of the hydrocodone or hydromorphone or solvate thereof in a solvent system comprising a water miscible solvent and water to form a second slurry; and
isolating a crystalline precipitate of the pharmaceutically acceptable salt of the hydrocodone or hydromorphone or solvate thereof from the second slurry.

40. The method of claim 39, wherein the isolating comprises
drying the crystalline precipitate of the pharmaceutically acceptable salt of the hydrocodone or hydromorphone or solvate thereof under humidified compressed air, humidified nitrogen, or humidified argon.

* * * * *